United States Patent [19]

Linemeyer et al.

[11] Patent Number: 5,401,832
[45] Date of Patent: Mar. 28, 1995

[54] BRAIN DERIVED AND RECOMBINANT ACIDIC FIBROBLAST GROWTH FACTOR

[75] Inventors: David L. Linemeyer, Westfield, N.J.; Linda J. Kelly, Yonkers, N.Y.; Guillermo Gimenez-Gallego, Jersey City; Kenneth A. Thomas, Jr., Chatham, both of N.J.

[73] Assignee: Merck & Co., Inc., Rahway, N.J.

[21] Appl. No.: 951,365

[22] Filed: Sep. 25, 1992

Related U.S. Application Data

[63] Continuation of Ser. No. 765,472, Sep. 25, 1991, abandoned, which is a continuation of Ser. No. 654,397, Feb. 8, 1991, abandoned, which is a continuation of Ser. No. 190,293, May 4, 1988, abandoned, which is a continuation-in-part of Ser. No. 868,473, May 30, 1986, abandoned, which is a continuation-in-part of Ser. No. 774,359, Sep. 12, 1985, abandoned, which is a continuation-in-part of Ser. No. 685,923, Dec. 24, 1984, abandoned, and Ser. No. 54,991, Jun. 4, 1987, abandoned, which is a continuation-in-part of Ser. No. 884,460, Jul. 11, 1986, abandoned.

[51] Int. Cl.⁶ ............................................. A61K 37/36
[52] U.S. Cl. ..................................... 530/399; 530/402
[58] Field of Search ................... 530/402, 399; 514/12

[56] References Cited

U.S. PATENT DOCUMENTS

| | | | |
|---|---|---|---|
| 4,296,100 | 10/1981 | Franco | 424/108 |
| 4,378,347 | 3/1983 | Franco | 424/108 |
| 4,443,546 | 4/1984 | Sterman et al. | 435/240 |
| 4,444,760 | 4/1984 | Thomas | 530/399 |
| 4,546,500 | 10/1985 | Bell | 435/1 |
| 4,868,113 | 9/1989 | Jaye et al. | 435/172.3 |

FOREIGN PATENT DOCUMENTS

| | | |
|---|---|---|
| 0131150 | 1/1985 | European Pat. Off. |
| 0142344 | 5/1985 | European Pat. Off. |
| 0225701 | 6/1987 | European Pat. Off. |
| WO87/01728 | 3/1987 | WIPO |
| WO87/05332 | 9/1987 | WIPO |

OTHER PUBLICATIONS

Conn, G. and Hatcher, V., Biochemical and Biophysical Res. Comm. vol. 124, No. 1, 1984; pp. 262-268.
Lobb, R. et al. Biochemical and Biophysical Res. Commun vol. 131, No. 2, 1985 pp. 586-592.
Bohlen P. et al. FEBS 2547, vol. 185, No. 1, Jun. 1985.
Thornton, et al., Science 222: 623-625 (1983).
Maciag, et al., Science 225: 932-935 (1984).
Schreiber, et al., Proc. Natl. Acad. Sci. USA 82: 6138-6142 (1985).

(List continued on next page.)

*Primary Examiner*—Howard E. Schain
*Attorney, Agent, or Firm*—John W. Wallen, III; Jack L. Tribble; Paul D. Matukaitis

[57] ABSTRACT

Acidic fibroblast growth factor (aFGF) is isolated and purified from human brain tissue. The distinctive and complete amino acid sequences of both bovine and human aFGFs are determined and herein disclosed. Unique genes coding for these disclosed amino acid sequences are constructed. The bovine gene is derived from reverse translation of the aFGF amino acid sequence with unique restriction sites included while the human gene is derived by specific point mutations of the bovine gene. Each gene construct is inserted into an expression vector which is used to transform an appropriate host. The transformed host cells produce recombinant aFGF (r-aFGF), human or bovine, which is purified and has activity equivalent to the native protein. Both recombinant and purified brain-derived human and bovine aFGF are active mitogens for mesoderm and neuroectoderm-derived cells in culture, and promote wound healing of soft tissue, cartilaginous tissue and musculo-skeletal tissue. Acidic fibroblast growth factor, recombinant and purified brain-derived, is also useful for the growth of vascular endothelial cells and for coverage of polymeric vascular grafts; growth of such cultures on tubular supports for production of blood vessels for implantation; and stimulation or facilitation of blood vessel growth and repair in vivo.

2 Claims, 8 Drawing Sheets

OTHER PUBLICATIONS

Gospodarowicz and Chen, J. Cell. Physiol. 128: 475–484 (1986).
Anderson and Kingston, Proc. Natl. Acad. Sci, USA 80: 6838–6842 (1983).
Armelin, Proc. Nat. Acad. Sci. USA 70: 2702–2706 (1973).
Aviv and Leder, Proc. Natl. Acad. Sci. USA 69: 1408–1412 (1972).
Barritault et al, J. Neurosci. Res 8.: 477–490 (1982).
Beaucage and Caruthers, Tetrahedron Letters 22: 1859–1862 (1981).
Brosius, Gene 27: 161–172 (1984).
deBoer et al., Proc. Natl. Acad. Sci. USA 80: 21–25 (1983).
Esch et al., Proc. Natl. Acad. Sci. USA 6507–6511 (1985).
Gentz et al., Proc. Natl. Acad. Sci. USA 78: 4936–4940 (1981).
Gimenez-Gallego et al., Science 230: 1385–1388 (1985).
Gimenez-Gallego et al., Biochem. Biophys. Res. Comm. 135: 541–548 (1986).
Gospodarowicz et al, Natl. Cancer Inst. Monog. 48: 109–130 (1978).
Hoffman, Growth 4: 361–376 (1940).
Itakura et al., Science 198: 1056–1063 (1977).
Kuo et al., Fed. Proc. 44: 695 (1985).
Lemmon and Bradshaw, J. Cell. Biochem. 21: 195–208, (1983).
Lobb and Fett, Biochem. 23: 6296–6299 (1984).
Maniatis et al., Cell 15: 687–701 (1978).
Maniatis et al., Molecular Cloning, A Laboratory, Cold Spring Harbor N.Y. pp. 217–246, 270–294, 353–361 (1982).
Matteucci and Caruthers, J. Am. Chem. Soc. 103: 3185–3191 (1981).
Maxam and Gilbert, Proc. Natl. Acad. Sci. USA 74: 560–564 (1977).
Norris et al., Nucleic Acids Res. 11: 5103–5112 (1983).
O'Farrell, J. Biol. Chem. 250: 4007–4021 (1975).
Smithies et al., Science 202: 1284–1289 (1978).
Suggs et al., Proc. Natl. Acad. Sci. USA 78: 6613–6617 (1981).
Thomas et al., Proc. Natl. Acad. Sci, USA 81: 357–361 (1984).
Thomas et al., Proc. Natl. Acad. Sci. USA 82: 6409–6413 (1985).
Thomas and Gimenez-Gallego, TIBS 11: 81–84 (1986).
Thomas et al., J. Biol. Chem. 255: 5517–5520 (1980).
Trowell et al., J. Exp. Biol. 16: 60–70 (1939).
Wensink et al., Cell 3: 315–325 (1974).
Zoller and Smith, Methods in Enzymology 100: 468–500 (1983).
Zoller and Smith, DNA 3: 479–488 (1984).
Abraham et al., J. Cell Biochem. Supp. vol. O, No. 11 Part A p. 50 (1987).
Burgess et al. Proc. Natl. Acad. Sci. USA 83: 7216–7220 (1986).
Canalis et al., J. Clin. Invest. 79: 52–58 (1987).
Crabb et al., Biochem. 25: 4988–4993 (1986).
Fiddes et al., J. Cell Biochem. vol. O, No. 10, Part C p. 149 (1986).
Fourtanier et al., J. Invest. Dermatal. 87: 76–80 (1986).
Gautschi-Sova et al., Biochem. Biophys. Res. Comm. 140: 874–880 (1986).
Gimenez-Gallego et al. Biophys. Res. Comm. 138: 611–617 (1986).
Greisler et al., Tras. Am. Soc. Artif. Intern. Organs, vol. XXXII: 346–349 (1986).
Harper et al., Biochem. 25: 4097–4103 (1986).
Jaye et al., Science 233: 541–545 (1986).
Linemeyer et al., Bio/Tech. 5: 960–965 (1987).
Thomas et al., J. Prot. Chem. 6: 163–171 (1987).
Bohlen et al., Proc. Natl. Acad. Sci. USA 81: 5364–5368 (1984).
Esch et al., Biochem. Biophys. Res. Comm. 133: 554–562 (1985).
Gospodarowicz et al., Proc. Natl. Acad. Sci. USA 73: 4120–4124 (1976).
Gospodarowicz et al., J. Cell Biol. 97: 1677–1685 (1983).
Schreiber et al., J. Cell Biol. 101: 1623–1626 (1985).
Tseng et al., Dur. J. Biochem. 122: 355–360 (1982).
Vlodavsky et al., J. Cell Biol. 83: 468–486 (1979).
Alberts et al., *Molecular Biology of The Cell*, Garland Publishing, Inc., N.Y. 1983.
Gospodarowicz et al., *Proc. Natl. Acad. Sci.*, 81, 6963–6967, 1984.

```
                                  60
GLY-GLU-VAL-TYR-ILE-LYS-SER-THR-GLU-THR-GLY-GLN-PHE-LEU-ALA-MET-ASP-
```

```
         70                              80
THR-ASP-GLY-LEU-LEU-TYR-GLY-SER-GLN-THR-PRO-ASN-GLU-GLU-CYS-LEU-PHE-
```

```
         90                              100
LEU-GLU-ARG-LEU-GLU-GLU-ASN-HIS-TYR-ASN-THR-TYR-ILE-SER-LYS-LYS-HIS-
```

```
                          110
ALA-GLU-LYS-HIS-TRP-PHE-VAL-GLY-LEU-LYS-LYS-ASN-GLY-ARG-SER-LYS-LEU-
```

FIG. 1B 120                                           130
GLY-PRO-ARG-THR-HIS-PHE-GLY-GLN-LYS-ALA-ILE-LEU-PHE-LEU-PRO-LEU-PRO-
                                    |→ → → → → → → → → → →
                                    |←——— T2-11 ———————
————————————————— CNBr-1 ——————————————————————————
→ → → → → → → → → → → → → → → → → → → → → → → → → → →
———————————— HA-7 ————————————————
→ → → →
————————————————— V8-8 —————————————————

140
→ → →
VAL-SER-SER-ASP
→ → → →
——— T2-11 ——→|
— CNBr-1 ——|
→ → →
——— HA-7 ——→|
——— V8-8 ——→|

FIG.1C

BRAIN DERIVED AND RECOMBINANT ACIDIC FIBROBLAST GROWTH FACTOR

RELATED U.S. APPLICATION DATA

This is a continuation of application Ser. No. 07/765,472, (now abandoned) filed Sep. 25, 1991; which is a continuation of application Ser. No. 07/654,397, (now abandoned) filed Feb. 8, 1991; which is a continuation of U.S. Ser. No. 190,293, filed May 4, 1988, (now abandoned) which is a continuation-in-part of U.S. Ser. No. 868,473, filed May 30, 1986, (now abandoned) which in turn is a continuation-in-part of U.S. Ser. No. 774,359, filed Sep. 12, 1985 (now abandoned), which in turn is a continuation-in-part of U.S. Ser. No. 685,923, filed Dec. 24, 1984 (now abandoned) and U.S. Ser. No. 054,991, filed Jun. 4, 1987 (now abandoned) which in turn is a continuation-in-part of U.S. Ser. No. 884,460, filed Jul. 11, 1986 (now abandoned).

BACKGROUND OF THE INVENTION

Figure 1A:
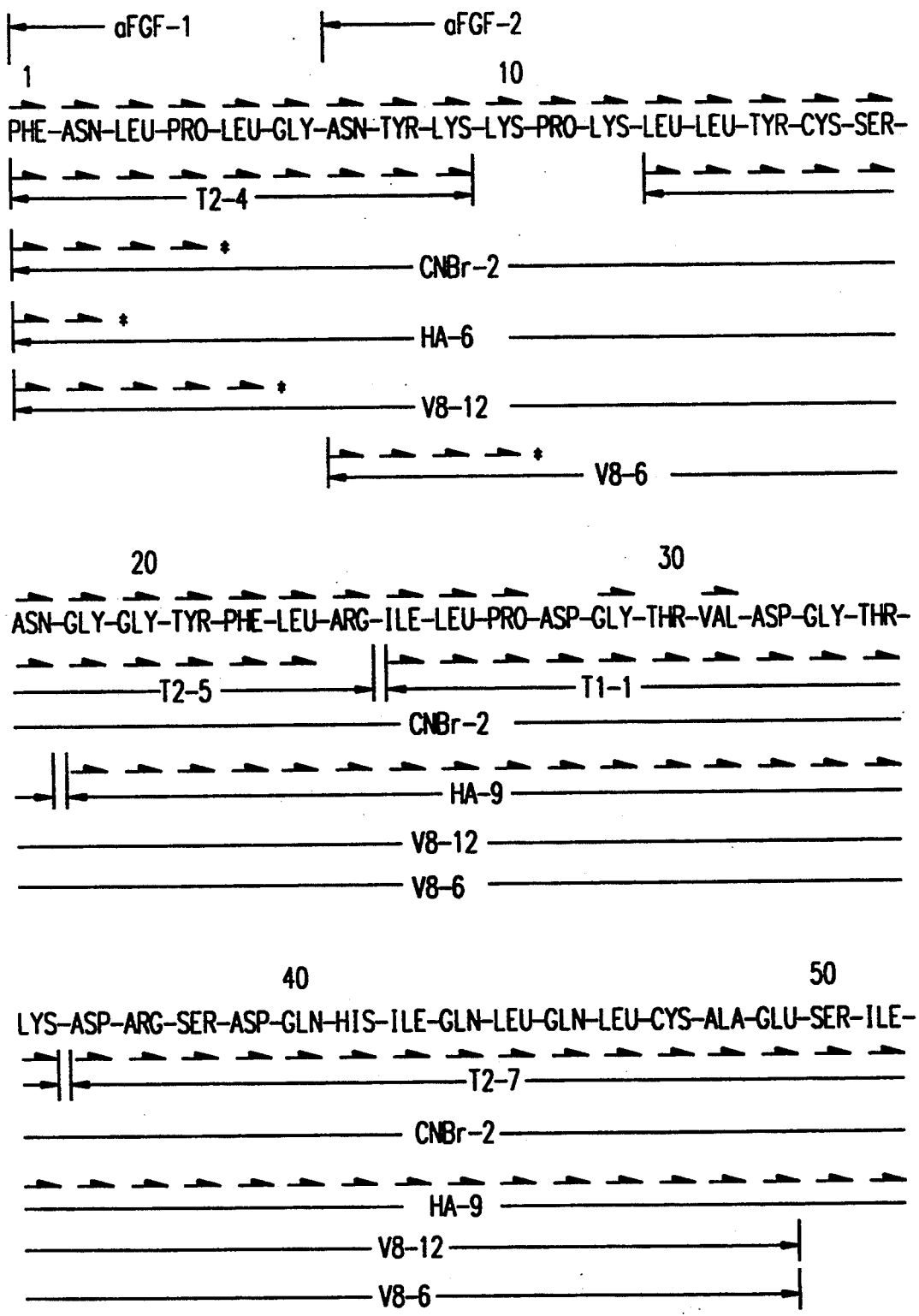
FIG. 1 is the complete amino acid sequence of bovine acidic fibroblast growth factor as determined from sequences of the amino and carboxy termini and overlapping peptides generated by proteolytic cleavages with trypsin (T), Staphylococcus aureus V8 Protease (V8), hydroxylamine (HA) and cyanogen bromide (CNBr).

The discovery of substances that control the growth of mammalian cells, especially human cells, and the mechanism by which they work is currently one of the major focuses of biomedical research concerned with tissue repair and wound healing. Fibroblast growth factors (FGFs), mitogens for various cell types including fibroblasts, have been identified and it has been suggested that they may induce mitosis which will result in tissue repair. Fibroblast mitogenic activity was initially observed with extracts of tissue from the central nervous system. Brain-derived fibroblast mitogens were first described by Trowell et al., J. Exp. Biol. 16: 60-70 (1939) and Hoffman, Growth 4: 361-376 (1940). It was subsequently shown that pituitary extracts also had potent mitogenic activity for fibroblasts, Armelin, Proc. Natl. Acad. Sci. USA 70: 2702-2706 (1973). Partial purification of both brain and pituitary fibroblast growth factor revealed copurification of mitogenic activity against a variety of types of differentiated cells including vascular endothelial cells, Gospodarowicz et al., Natl. Cancer Inst. Monogr. 48: 109-130 (1978).

Fibroblast growth factor was originally thought to be a single peptide derived from the limited proteolysis of myelin basic protein. It has recently been shown that FGF exists in two forms, acidic FGF (aFGF) and basic FGF (bFGF), and that both forms can be isolated and purified from mammalian brain, Thomas, et al., Proc. Natl. Acad. Sci. USA 81: 357-361 (1984), Lemmon and Bradshaw, J. Cell Biochem. 21:195-208 (1983). Numerous cell types respond to stimulation with either purified aFGF or bFGF to synthesize DNA and divide, including primary fibroblasts, vascular and corneal endothelial cells, chondrocytes, osteoblasts, myoblasts, smooth muscle cells, glial cells and neuroblasts, Esch et al., Proc. Natl. Acad. Sci. USA 82: 6507-6511 (1985); Kuo et al., Fed. Proc. 44: 695 (1985). Pure bovine brain-derived aFGF not only acts as a potent mitogen for vascular endothelial cells in culture but also induces blood vessel growth in vivo, Thomas, et al., Proc. Natl. Acad. Sci. USA 82: 6409-6413 (1985). The mitogenic activity of purified aFGF can also be used to promote wound healing, Thomas U.S. Pat. No. 4,444,760.

Acidic fibroblast growth factor was originally purified to homogeneity from bovine brain based on its mitogenic activity for BALB/c 3T3 fibroblasts, Thomas et al., Proc. Natl. Acad. Sci. USA 81: 357-361 (1984). This brain-derived growth factor has been repurified and renamed in multiple laboratories based both on its: mitogenic activity for vascular endothelial cells, astroglial cells and prostate epithelial cells (endothelial cell growth factor, astroglial growth factor 1 and prostatropin); source (retinal-derived growth factor, eye-derived growth factor II, brain-derived growth factor); and binding to heparin-Sepharose (class 1 heparin-binding growth factor or heparin-binding growth factor alpha) Thomas and Gimenez-Gallego, TIBS 11:81-84 (1986). The amino acid sequence of bovine aFGF has been determined, recognized to be highly homologous to basic FGF and perhaps related to the fibroblast mitogens interleukin 1-alpha and 1-beta, Gimenez-Gallego et al., Science 230: 1385-1388 (1985). The complete amino acid sequence of human aFGF has been determined from the purified protein, Gimenez-Gallego et al., Biochem. Biophy. Res. Comm. 138: 611-617 (1986), and from the gene, Jaye et al., Science 233: 541-545 (1986). Heretofore the availability of aFGF has been dependent upon the isolation and purification of the proteins from animal tissues, generally bovine. The unavailability of human aFGF has limited the use of aFGF as a therapeutic agent in humans. The present invention will allow the production of therapeutically significant amounts of highly purified human and bovine aFGF.

To date, the growth of vascular endothelial cells could only be accomplished using very high concentrations of fetal calf or adult bovine serum, 10 to 30%. The results were variable, depending on the particular lot of calf serum and the rate of cell growth was generally slow. Now, with brain-derived and recombinant aFGF, rapid endothelial cell growth rates are achieved with serum levels as low as 0 to 2%.

This novel method of reproducible stimulation of vascular endothelial cell growth, mediated by pure brain-derived and recombinant aFGF, permits the covering of synthetic polymeric vessels with non-thrombogenic vascular endothelial cells from a host animal, including human, whereby many or all of the clotting problems associated with synthetic vessel grafts are obviated. Endothelial cell stimulation with aFGF is also used for the production of vessels in vitro by growth of host vascular endothelial cells on tubular supports, for implantation back into the same host animal, including human, whereby immunological rejection of the implant will be obviated and the frequent limited supply of good vessels within the patient for transplant will be obviated. Tubular supports are coated in vitro with aFGF prior to implantation into a host animal. Following implantation endothelial cells migrate into and grow on the artificial surface producing in vivo artificial vessels. Acidic fibroblast growth factor can also be used for the stimulation or facilitation of blood vessel growth and repair in vivo, whereby the flow of blood to tissues deprived of adequate oxygen and/or other blood borne components is increased.

OBJECTS OF THE INVENTION

It is, accordingly, an object of the present invention to provide an amino acid sequence and a nucleotide base sequence for both bovine aFGF and human aFGF. Another object is to produce genes coding for the specific aFGFs and incorporate the genes into appropriate cloning vectors. A further object is to transform an appropriate host with each of the recombinant vectors and to induce expression of the specific aFGF genes. Another object is to isolate and purify biologically active bovine aFGF and human aFGF. A further object is the use of aFGF to stimulate soft tissue, musculo-skeletal and cartilaginous tissue repair. A further object is to use aFGF to stimulate vascular endothelial cells in culture for coverage of polymeric vascular grafts and growth of vascular endothelial cells on tubular supports for the production of blood vessels for implantation. Another object is to treat tubular supports in vitro with aFGF and implant in a host for the production of artificial vessels. Another object is to use aFGF to stimulate and facilitate growth and repair of blood vessels in vivo. These and other objects of the present invention will be apparent from the following description.

SUMMARY OF THE INVENTION

Acidic fibroblast growth factor (aFGF) is isolated and purified from human brain tissue. The distinctive amino acid sequences of both bovine and human aFGFs are determined and herein disclosed. Unique genes coding for these disclosed amino acid sequences are constructed. The bovine gene is derived from reverse translation of the aFGF amino acid sequence with unique restriction sites included while the human gene is derived by specific point mutations of the bovine gene. Each gene construct is inserted into an expression vector which is used to transform an appropriate host. The transformed host cells produce recombinant aFGF (r-aFGF), human or bovine, which is purified and has activity equivalent to the native protein. Both recombinant and brain-derived human and bovine aFGF are active mitogens for mesoderm-derived cells such as vascular endothelial cells in culture, and promote wound healing of soft tissue, cartilaginous tissue and musculo-skeletal tissue. Acidic fibroblast growth factor, recombinant and purified brain-derived is also useful for the growth of the vascular endothelial cells and for coverage of polymeric vascular grafts; growth of such cultures on tubular supports for production of blood vessels for implantation; and stimulation or facilitation of blood vessel growth and repair in vivo.

DETAILED DESCRIPTION OF THE INVENTION

Acidic fibroblast growth factor exists in various microheterogeneous forms which are isolated from the various tissue sources and cell types known to contain aFGF. Microheterogeneous forms as used herein refer to a single gene product, that is a peptide produced from a single gene unit of DNA, which is structurally modified at the mRNA or following translation. These structural modifications, however, do not result in any significant alterations of biological activity of the peptide. Biological activity and biologically active are used interchangably and are herein defined as the ability of native or recombinant aFGF to stimulate DNA synthesis in quiescent Balb/c 3T3 fibroblasts as described below, to stimulate any of the cell types described above or to carry out any of the functions described in the art. The modifications may take place either in vivo or during the isolation and purification process. In vivo modification results from, but is not limited to, proteolysis, glycosylation, phosphorylation or acetylation at the N-terminus. Proteolysis may include exoproteolysis wherein one or more terminal amino acids are sequentially, enzymatically cleaved to produce microheterogeneous forms which have fewer amino acids than the original gene product. Proteolysis may also include endoproteolytic modification that results from the action of endoproteases which cleave the peptide at specific locations within the amino acid sequence. Similar modifications can occur during the purification process which also results in production of microheterogeneous forms. The most common modification occuring during purification is proteolysis which is generally held to a minimum by the use of protease inhibitors. Under most conditions a mixture of microheterogeneous forms are present following purification of native aFGF. Native aFGF refers to aFGF isolated and purified from tissues or cells that contain aFGF.

The unique amino acid sequences for the predominant native bovine and human microheterogeneous forms of aFGF have been determined. Sequence determinations of the reduced and carboxymethylated bovine protein have revealed two amino termini. The longer sequence, the 140 amino acid form, contains six amino terminal residues not found on the shorter 134 amino acid form. The relative amounts of these two microheterogeneous forms of aFGF vary from one purification to another but are closely correlated in amount to the abundance of the two bands of protein previously seen by electrophoresis in SDS polyacrylamide gels (Thomas, et al., *Proc. Natl. Acad. Sci. USA*, 81, 357-361 (1984)). As expected, the amount of the longer amino terminal sequence correlates with the relative quantity of the higher mass band on the SDS gels. If the length of the polypeptide chain at the amino termini is the only difference between the two microheterogeneous forms observed on the SDS gels, then the mass difference between them is 642 daltons, rather than the previously estimated 200 daltons based on SDS gel migration distances. It is assumed that the amino terminal heterogeneity is the result of limited proteoysis either in vivo or during purification.

The complete reduced and carboxymethylated bovine and human proteins and peptides derived from them were purified by reversed-phase HPLC chromatography and sequenced on an Applied Biosystems 470A microsequencer. The complete amino acid sequence of bovine aFGF was determined from sequences of the amino termini and overlapping peptides generated by proteolytic cleavages with trypsin (T), *Staphylococcus aureus* V8 Protease (V8), hydroxylamine (HA) and cyanogen bromide (CNBr). The carboxyl terminal sequence of the whole protein was confirmed by timed carboxypeptidase A digestion. The complete amino acid sequence of the 140-amino acid residue and the 134-amino acid residue bovine aFGF is shown in FIG. 1. Peptide sequences that were prematurely terminated because they were recognized to begin at one of the two previously determined amino termini are marked with asterisks following the last degradation cycle. Peptides are identified by double headed arrows on lines spanning their full length. Single headed arrows above the amino acid sequence pointing to the right denote the residues identified by analysis of the whole protein. Similar arrows above the labeled lines spanning the lengths of the individual peptides signify the residues identified from degradations of these purified peptides. Arrows pointing to the left above the end of the sequence denote residues confirmed by carboxypeptidase A digestion of the whole reduced and carboxymethylated protein. Tryptic peptides denoted by T1 and T2 were obtained after 21- and 6-hour digestions.

Figure 2A:
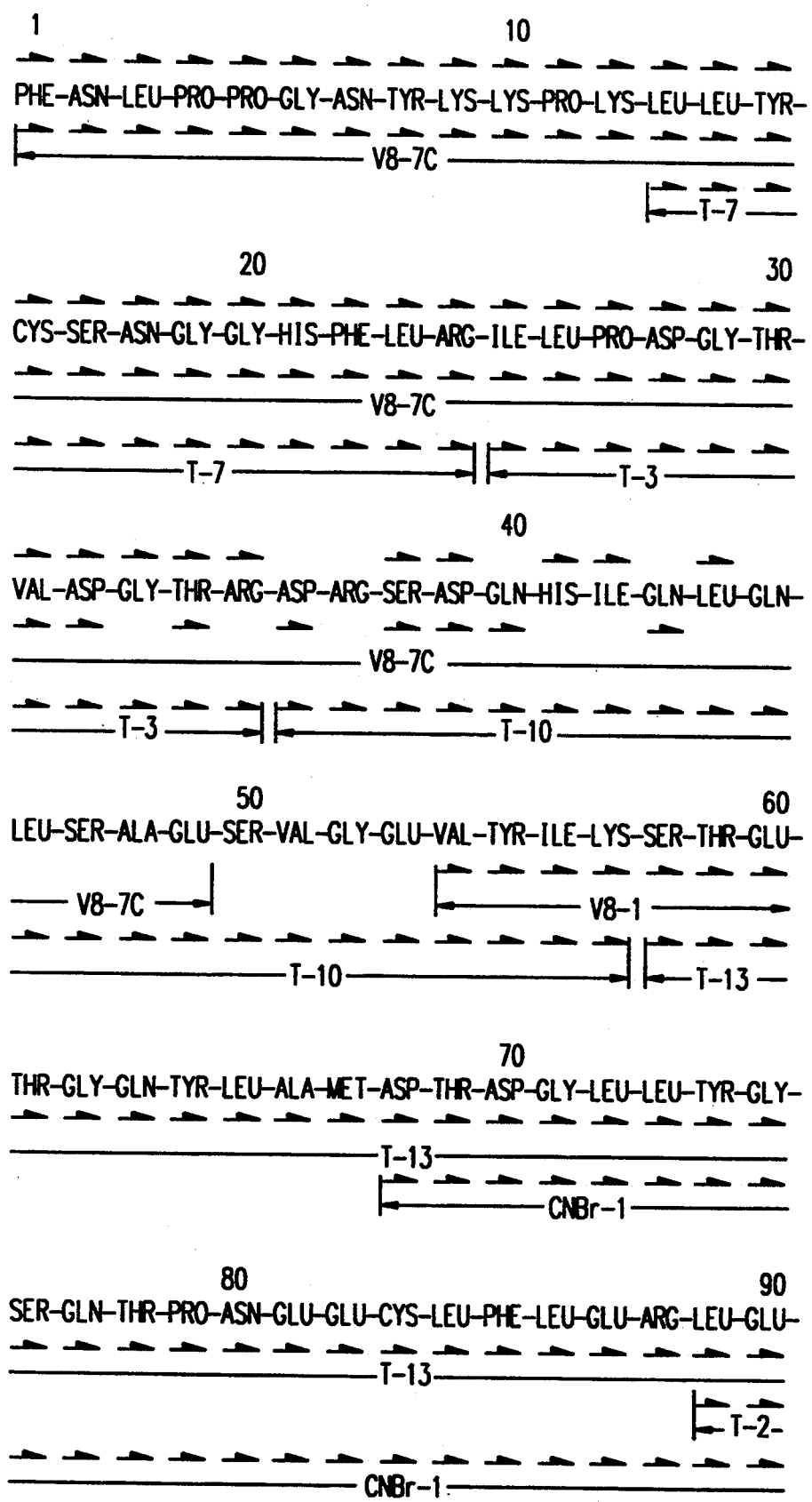
FIG. 2 is the amino acid sequence of human acidic fibroblast growth factor as determined from sequences of the amino and carboxy termini and overlapping peptides generated by proteolytic cleavages with trypsin (T), Staphylococcus aureus V8 Protease (V8), and cyanogen bromide (CNBr).
Figure 2B:
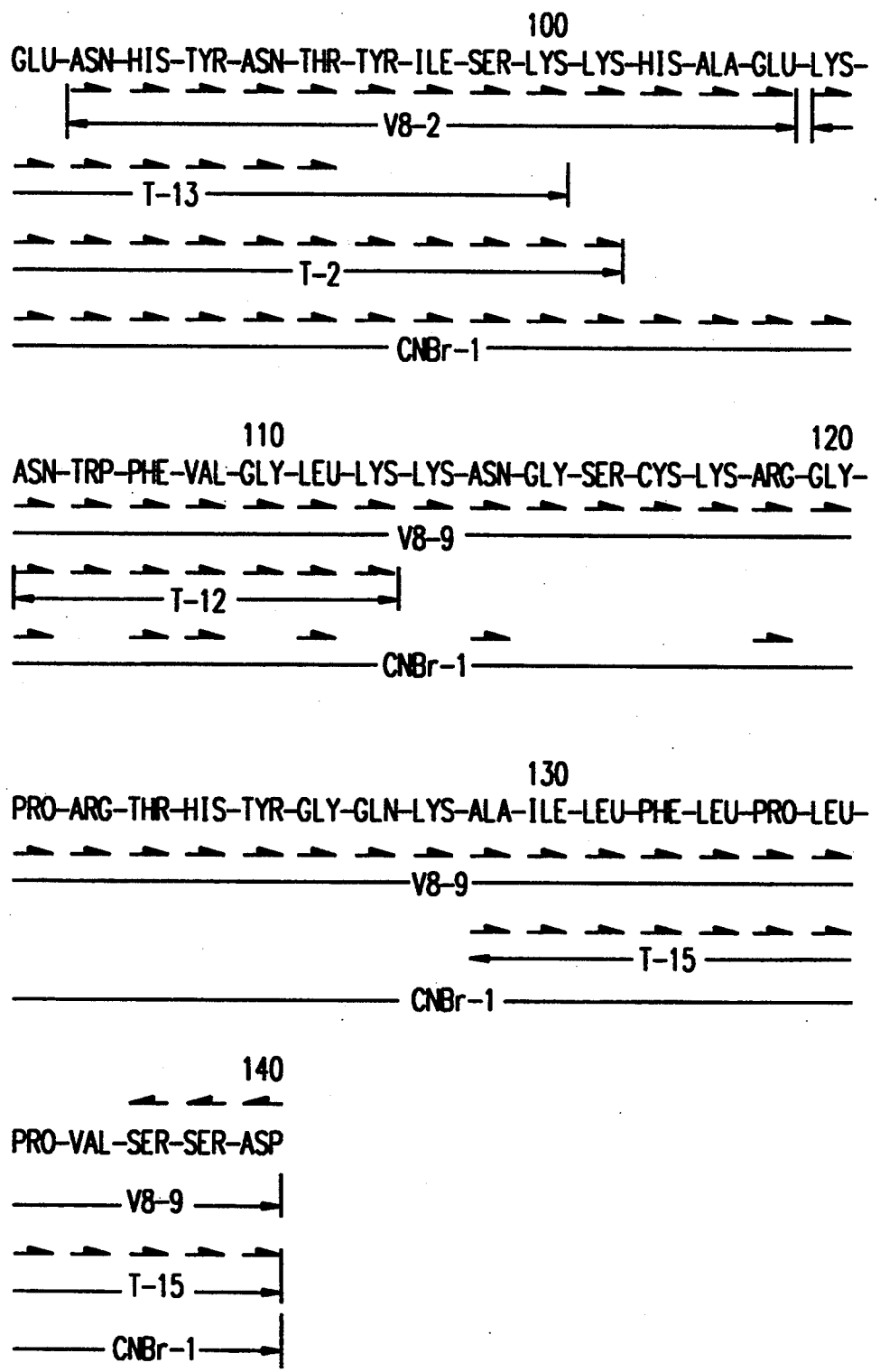

The complete 140-residue amino acid sequence of human brain-derived acidic fibroblast growth factor was derived from an amino terminal sequence and sequences of overlapping peptides generated from it by proteolysis with trypsin (T), Staphylococcus aureus V8 protease (V8), or cyanogen bromide (CNBr) with confirmation of the carboxyl terminal residues by timed carboxypeptidase A digestion of the whole protein. The complete amino acid sequence of human 140-amino acid residue and 139-amino acid residue aFGF is shown in FIG. 2.

In a search of the current Dayhoff protein data bank, bovine and human aFGFs are unique compared to the approximately 2000 protein sequences contained in that list.

The invention is contemplated to include all mammalian microheterogeneous forms of acidic fibroblast growth factor. The preferred embodiments include bovine and human microheterogeneous forms of aFGF. The most preferred microheterogeneous forms of bovine aFGF include a 154 amino acid form, a 140 amino acid form and a 134 amino acid form. The 140 amino acid form as shown in FIG. 1 is the most preferred of the bovine species. The 154 amino acid form includes the following additional amino acids; Ala—Glu—Gly—Glu—Thr—Thr—Thr—Phe—Thr—Ala—Leu—Thr—Glu—Lys, with the carboxyl terminus Lys attached to the amino terminal Phe at the first position of the 140 amino acid form. The additional amino acids of the 154 amino acid form are numbered from the N-terminal Ala, -14, to the carboxyl terminal Lys, -1. The 134 amino acid form is identical to the 140 amino acid form except that the first 6 amino acids of the amino terminus have been removed as shown in FIG. 1. When native aFGF is isolated, from any aFGF producing tissue or cells, the relative amounts of these microheterogeneous forms vary depending on the process used but generally contain at least two of these forms.

Human aFGF exhibits a similar microheterogeneity to that of bovine aFGF. The most preferred. microheterogeneous forms of human aFGF include a 154 amino acid form, a 140 amino acid form and a 139amino acid form. The human 140 amino acid form differs from the bovine form by eleven amino acids, as shown in TABLE 5. The 154 amino acid form contains the exact sequence of the human 140 amino acid form plus the 14 additional amino acids associated with the bovine 154 amino acid form, with one exception. The amino acid at the fifth position of the N-terminus or at the -10 position as determined from the 140 amino acid Phe N-terminus in the human form is isoleucine and is substituted for the threonine in the bovine form. The additional 14 amino acid human N-terminal sequence is: Ala—Glu—Gly—Glu—Ile—Thr—Thr—Phe—Thr—Ala—Leu—Thr—GluLys. The additional amino acids of the 154 amino acid form are numbered from N-terminal Ala, -14, to the carboxyl terminal Lys, -1. A third form of human aFGF contains 139 amino acids and is equivalent to the human 140 amino acid form with the amino terminal phenylalanine removed. The amino terminal asparagine residue may be deamidated to aspartic acid in the 139 amino acid form of human aFGF. The 140 and 139 amino acid forms are the most preferred forms of the human microheterogeneous forms.

Mammalian recombinant aFGF (r-aFGF) is produced by cloning the natural gene from either the genomic DNA or cDNA, or by construction of a gene for one of the microheterogeneous forms of the protein based on the known amino acid sequences of these microheterogeneous forms of aFGF from mammalian species including man. Genomic DNA is extracted from any animal cell or mRNA is extracted primarily from either mammalian brain or any other aFGF-producing tissue or cell type and prepared for cloning by either random fragmentation of high-molecular-weight DNA following the technique of Maniatis et al., Cell 15: 687–701 (1978) or by cleavage with a restriction enzyme by the method of Smithies et al., Science 202: 1284–1289 (1978). The genomic DNA is then incorporated into an appropriate cloning vector, generally E. coli lambda phage, see Maniatis et al., Molecular Cloning, A Laboratory Manual, Cold Spring Harbor Laboratory, Cold Spring Harbor, N.Y. (1982).

To obtain cDNA for aFGF, poly (A)-containing RNA is extracted from cells that express aFGF by the method of Aviv and Leder, Proc. Natl. Acad. Sci. 69: 1408–1412 (1972). The cDNA is prepared using reverse transcriptase and DNA polymerase using standard techniques, as described in Manjarls et al., Molecular Cloning, a Laboratory Manual, Cold Spring Harbor Laboratory, Cold Spring Harbor, N.Y. (1982). The cDNA is tailed and cloned into an appropriate vector, usually pBR322, by a technique similar to that of Wensink, et al., Cell 3: 315–325 (1974).

The clonal genomic DNA or cDNA libraries are screened to identify the clones containing aFGF sequences by hybridization with an oligonucleotide probe. The sequence of the oligonucleotide hybridization probe is based on the determined amino acid sequence of aFGF. Manjarls et al. supra, Anderson and Kingston, Proc. Natl. Acad. Sci. USA 80: 6838–6842 (1983) and Suggs et al., Proc. Natl. Acad. Sci. USA 78: 6613–6617 (1981) describe various procedures for screening genomic and cDNA clones.

The preferred procedure for obtaining a gene for mammalian aFGF is to synthesize the gene. The gene may be synthesized based on the amino acid sequence of a microheterogeneous form of aFGF obtained from any mammal including man. The preferred method is to use the bovine amino acid sequence for aFGF and chemically point mutate the base sequence to produce the genes for other species.

The synthetic genes are based on the determined bovine amino acid sequence described herein. The unique nucleotide sequence of the 140 amino acid form of bovine aFGF is derived from reverse translation of the amino acid sequence by a technique similar to that of Itakura et al., Science 198: 1056–1063 (1977). The various novel nucleotide sequences corresponding to the native amino acid sequence of bovine aFGF are shown in the following table:

TABLE 1

| | | | | | 5 | | | | | 10 | | | | 15 | | | | | 20 |
|---|---|---|---|---|---|---|---|---|---|---|---|---|---|---|---|---|---|---|---|
| Phe TTQ | Asn AAQ | Leu CTN/TTP | Pro CCN | Leu CTN/TTP | Leu CTN/TTP | Gly GGN | Asn AAQ | Tyr TAQ | Lys AAP | Lys AAP | Pro CCN | Leu CTN/TTP | Leu CTN/TTP | Tyr TAQ | Cys TGQ | Ser TCN/AGQ | Asn AAQ | Gly GGN | Gly GGN |
| Tyr TAQ | Phe TTQ | Leu CTN/TTP | Arg CGN/AGP | Ile ATQ/ATA | Leu CTN/TTP | Leu CTN/TTP | Pro CCN | Asp GAQ | Gly GGN | Thr ACN | Val GTN | Asp GAQ | Thr ACN | Lys AAP | Asp GAQ | Arg CGN/AGP | Ser TCN/AGQ | Asp GAQ | Gln CAP |
| His CAQ | Ile ATQ/ATA | Gln CAP | Leu CTN/TTP | Gln CAP | Leu CTN/TTP | Cys TGQ | Ala GCN | Glu GAP | Ser TCN/AGQ | Ile ATQ/ATA | Gly GGN | Glu GAP | Val GTN | Tyr TAQ | Ile ATQ/ATA | Lys AAP | Ser TCN/AGQ | Thr ACN | Glu GAP |
| Thr ACN | Gly GGN | Gln CAP | Phe TTQ | Leu CTN/TTP | Ala GCN | Met ATG | Asp GAQ | Thr ACN | Asp GAQ | Asp GAQ | Ile ATQ/ATA | Asn AAQ | Leu CTN/TTP | Tyr TAQ | Ser TCN/AGQ | Gln CAP | Thr ACN | Pro CCN | Asn AAQ |
| Glu GAP | Glu GAP | Leu CTN/TTP | Leu CTN/TTP | Phe TTQ | Leu CTN/TTP | Glu GAP | Arg CGN/AGP | Leu CTN/TTP | Leu CTN/TTP | Glu GAP | Gly GGN | Asn AAQ | His CAQ | Gly GGN | Thr ACN | Tyr TAQ | Ile ATQ/ATA | Ser TCN/AGQ | Lys AAP |
| Lys AAP | His CAQ | Ala GCN | Glu GAP | Lys AAP | His CAQ | Trp TGG | Phe TTQ | Arg CGN/AGP | Val GTN | Gly GGN | Leu CTN/TTP | Lys AAP | Lys AAP | Asn AAQ | Arg CGN/AGP | Ser TCN/AGQ | Lys AAP | Ser TCN/AGQ | Lys AAP |
| Pro CCN | Arg CGN/AGP | Thr ACN | His CAQ | Phe TTQ | Gly GGN | Gln CAP | Lys AAP | Ala GCN | Ile ATQ/ATA | Leu CTN/TTP | Leu CTN/TTP | Phe TTQ | Leu CTN/TTP | Leu CTN/TTP | Pro CCN | Val GTN | Lys AAP | Ser TCN/AGQ | Gly GGN |
| | | | | Phe TTQ | | | | | | Ile ATQ/ATA | Leu CTN/TTP | Leu CTN/TTP | Leu CTN/TTP | Leu CTN/TTP | Pro CCN | Pro CCN | Ser TCN/AGQ | Ser TCP/AGQ | Asp GAQ |

Where
- Q=C or T,
- P=A or G, and
- N=A, T, C, or G

The nucleotide sequence of the present invention incorporates the following characteristics; codons preferred by *Escherichia coli* and mammalian cells where possible, elimination of sequences with multiple complementarities, incorporation of unique restriction sites throughout the gene, terminal restriction enzyme sticky ends for ease of inserting the gene into plasmids, a centrally located unique restriction site to allow assembly of the gene in two halves, preferably an N-terminal methionine codon for a translational start site, and tandem translational stop codons.

While the following description and examples illustrate the present invention with respect to a particular nucleotide sequence for bovine aFGF, it is to be understood that the present invention includes any of the permutations listed in Table 1. The following table contains the preferred nucleotide sequence:

TABLE 2

| | |
|---|---|
| TTCAATCTGCCACTGGGTAATTACAAAAAGCCAAAGCTTCTTTACTGCTCTAACGGTGGT | 60 |
| TACTTTCTCCGCATCCTGCCAGATGGTACCGTGGACGGCACCAAAGATCGTTCTGATCAA | 120 |
| CATATTCAACTGCAGCTGTGCGCCGAATCTATCGGTGAAGTTTACATCAAATCTACCGAA | 180 |
| ACTGGTCAATTCCTTGCCATGGACACTGATGGCCTGCTGTACGGATCCCAGACCCCAAAC | 240 |
| GAGGAGTGCCTTTTCCTGGAGCGCCTGGAGGAAAACCATTACAACACCTACATCTCTAAA | 300 |
| AAGCATGCTGAGAAACATTGGTTCGTAGGCCTTAAGAAAAATGGCCGCTCTAAACTGGGC | 360 |
| CCTCGTACTCACTTTGGTCAAAAAGCTATCCTGTTCCTGCCACTGCCAGTGAGCTCTGAC | 420 |

The gene is constructed with a leader portion containing a single restriction enzyme cleavage site and an N-terminal methionine codon for a translational start site. The gene also contains a tail containing tandem translational stop codons and two restriction enzyme cleavage sites. The complementary characteristic of DNA allows a choice of base sequences which in turn allows for the incorporation of unique restriction enzyme cleavage sites throughout the gene. The preferred gene base sequence with the location of the restriction enzyme cleavage sites is shown in the following table:

TABLE 3

```
                    1                              10
          MetPheAsnLeuProLeuGlyAsnTyrLysLysProLysLeuLeuTyrCysSer
                                    [1]
     1                   20                   40                  .       60
     AATTCATGTTCAATCTGCCACTGGGTAATTACAAAAAGCCAAAGCTTCT TTACTGCTC TA
         GTACAAGTTAGACGGTGACCCATTAATGTTTTTCGGTTTCGAAGA AATGACGAG AT
     |                          [2]                            |
    (EcoRI)                                               HindIII 20                          30
     AsnGlyGlyTyrPheLeuArgIleLeuProAspGlyThrValAspGlyThrLysAspArgSer
                                    [3]
                     .       80                   .      100            .       120
     ACGGTGGTTACTTTCTCCGCATCCTGCCAGATGGTACCGTGGACGGCA CCAAAGATCG TTCT
     TGCCACCAATGAAAGAGGCGTAGGACGGTCTACCATGGCACCTGCCGT GGTTTCTAGC AAGA
                    [4]                          |
                                               KpnI 40                          50
     AspGlnHisIleGlnLeuGlnLeuCysAlaGluSerIleGlyGluValTyrIleLys
                                    [5]
                     .      140                   .      160            .       180
     GATCAACATATTCAACTGCAGCTGTGCGCCGAATCTATCGGT GAAGTTTAC ATCAAAT
     CTAGTTGTATAAGTTGACGTCGACACGCGGCTTAGATAGCCA CTTCAAATG TAGTTTA
     |                 |    |         [6]     |
     BclI              PstI PvuII             HinfI 60                   70
     SerThrGluThrGlyGlnPheLeuAlaMetAspThrAspGlyLeuLeuTyrGlySerGlnThr
                                    [7]
                     .      200                   .      220            .       240
     CTACCGAAACTGGTCAATTCCTTGCCATGGACACTGATGGCCTGCTGTACG GATC CCAGACC
     GATGGCTTTGACCAGTTAAGGAACGGTACCTGTGACTACCGGACGACATGC CTAG GGTCTGG
                                 [8]     |                         |
                                        NcoI                     BamHI 80                          90
     ProAsnGluGluCysLeuPheLeuGluArgLeuGluGluAsnHisTyrAsnThrTyr
                                    [9]
                     .      260                   .      280            .       300
     CCAAACGAGGAGTGCCTTTTCCTGGAGCGCCTGGAGGAAAA CCATTACAAC ACCTACA
     GGTTTGCTCCTCACGGAAAAGGACCTCGCGGACCTCCTTTT GGTAATGTTG TGGATGT
                                 [10]            |
                                               HaeII 100                         110
     IleSerLysLysHisAlaGluLysHisTrpPheValGlyLeuLysLysAsnGlyArgSerLys
                                    [11]
```

TABLE 3-continued

```
                320                    340                      360
TCTCTAAAAAGCATGCTGAGAAACATTGGTT|CGTAGGCC  TTAAGAAAAATGGCCGCTCTAAA
AGAGATTTTTCGTACGACTCTTTGTAACCAA GCATCCGG|AATTCTTTTTACCGGCGAGATTT
        |          [12]                 |
      SphI                             StuI 120                          130
LeuGlyProArgThrHisPheGlyGlnLysAlaIleLeuPheLeuProLeuProValSer
    [13]                        [15]
                380                    400                      420
CTGGGCCCTCGTACTCACTTTG|GTCAAAAAGC TATCCTGTTCCTGCCACTGCCAGTGAGCT
GACCCGGGAGCATGAGTGAAAC CAGTTTTTCG|ATAGGACAAGGACGGTGACGGTCACTCGA
     |       [14]                                      [16]    |
    ApaI                                                      SacI

140
SerAsp..
            440
CTGACTAATAGATATCG         440
GACTGATTATCTATAGCAGCT
     |            |
   EcoRV       (SalI)
```

The gene sequence for each strand of the double-stranded molecule is randomly divided into 8 nucleotide sequences. The oligonucleotides are constructed with overlapping ends to allow the formation of the double-stranded DNA. The following table contains one of a multitude of oligonucleotide arrangements that is used to produce the bovine aFGF gene.

TABLE 4

| | 10 | 20 | 30 | 40 | 50 | | |
|---|---|---|---|---|---|---|---|
| OLIGO-1 5' | AATTCAGTT | CAATCTGCCA | CTGGGTAATT | ACAAAAAGCC | AAAGCTCTT | TACTGCTC 3' | 58 |
| OLIGO-2 5' | AGAAGCTTTG | GCTTTTTGTA | ATTACCCAGT | GGCAGATTGA | ACATG 3' | | 45 |
| OLIGO-3 5' | TAACGGTGGT | TACTTTCTCC | GCATCCTGCC | AGATGGTACC | GTGGACGGCA | CCAAAGATCG 3' | 60 |
| OLIGO-4 5' | TGCCGTCCAC | GGTACCATCT | GGCAGGATGC | GGAGAAAGTA | ACCACCGTTA | GAGCAGTTA 3' | 59 |
| OLIGO-5 5' | TTCTGATCAA | CATATTCAAC | TGCAGCTGTG | CGCCGAATCT | ATCGGT 3' | | 46 |
| OLIGO-6 5' | GTAAACTTCA | CCGATAGATT | CGGCGCACAG | CTGCAGTTGA | ATATGTTGAT | CAGAACGATC 3' | 60 |
| OLIGO-7 5' | GAAGTTTACA | TCAAATCTAC | CGAAACTGGT | CAATTCCTTG | CCATGGACAC | TGATGGCCTG 3' | 60 |
| OLIGO-8 5' | GATCCGTACA | GCAGGCCATC | AGTGTCCATG | GCAAGGAATT | GACCAGTTTC | GGTAGATTTG 3' | 60 |
| OLIGO-9 5' | GATCCCAGAC | CCCAAACGAG | GAGTGCCTTT | TCCTGGAGCG | CCTGGAGGAA | AA 3' | 52 |
| OLIGO-10 5' | GTTGTAATGG | TTTTCCTCCA | GGCGCTCCAG | GAAAAGGCAC | TCCTCGTTTG | GGGTCTGG 3' | 58 |
| OLIGO-11 5' | CCATTACAAC | ACCTACATCT | CTAAAAGCA | TGCTGAGAAA | CATTGGTT 3' | | 48 |
| OLIGO-12 5' | GGCCTACGAA | CCAATGTTTC | TCAGCATGCT | TTTTAGAGAT | GTAGGT 3' | | 46 |
| OLIGO-13 5' | CGTAGGCCTT | AAGAAAAATG | GCCGCTCTAA | ACTGGGCCT | CGTACTCACT | TTG 3' | 53 |
| OLIGO-14 5' | GCTTTTTGAC | CAAAGTGAGT | ACGAGGGCCC | AGTTTAGAGC | GGCCATTTT | CTTAA 3' | 55 |
| OLIGO-15 5' | GTCAAAAAGC | TATCCTGTTC | CTGCCACTGC | CAGTGAGCTC | TGACTAATAG | ATATCG 3' | 56 |
| OLIGO-16 5' | TCGACGATAT | CTATTAGTCA | GAGCTCACTG | GCAGTGGCAG | GAACAGGATA 3' | | 50 |

The oligonucleotides illustrated in Table 4 are presented merely as an example of oligonucleotide sub-units and should not be construed as limiting thereto. The composite base sequence showing the overlap and arrangement of the oligonucleotides is illustrated in Table 3.

The bovine gene is assembled in 2 steps: first, the half corresponding to the N-terminal portion of the protein; and second, the C-terminal half. Generally, the oligonucleotides are kinased with T4 polynucleotide kinase in the presence of either adenosine triphosphate (ATP) or $^{32}$P-labelled ATP. In the first reaction of each step the oligonucleotides which make up one strand of the gene are kinased with the exception of the most 5' oligonucleotide. In the second reaction the oligonucleotides which make up the second strand are kinased, with the exception of the most 5' oligonucleotide. When kinased oligonucleotides are used, about 1 pmole of the $^{32}$P-labelled oligonucleotide is added for later identification of the products. Annealing is carried out in an appropriate buffer, such as one containing but not limited to about 60 mM tris-(hydroxymethyl)aminomethane (Tris), about pH 7.6, about 5 mM dithiothreitol (DTT), about 10 mMMgCl$_2$, and about 30 µM ATP at about 90° C. for about 4 minutes followed by a rapid transfer to about 60° C. and a slow cooling to about 30° C. Ligation is carried out in an appropriate buffer, such as one containing, but not limited to, about 60 mM TRIS, about pH 7.6, about 10 mM DTT, about 10 mM MgCl$_2$, about 1 mM ATP, and about 0.03 units T4 DNA ligase at about 20° C. for about 1 and ½ hour.

The ligated oligonucleotides are purified by polyacrylamide gel electrophoresis following ethanol precipitation. The oligonucleotides are redissolved in a buffer containing about 20 µl of about 80% formamide, about 50 mM Tris-borate, about pH 8.3, about 1 mM ethylenediaminetetraacetic acid (EDTA), about 0.1% (w/v) xylene cyanol, and about 0.1% (w/v) bromophenol blue. Each sample is heated at about 90° C. for about 3 minutes and electrophoresed in about a 10% urea-polyacrylamide gel at about 75 watts for about 5 hours. The 231 base N-terminal bands are removed, combined and eluted at about 4° C. in about 0.5M ammonium acetate containing about 1 mM EDTA at about pH 8. The 209 base C-terminal bands are treated in the same manner.

The synthetic gene sequences coding for either the N-terminal or the C-terminal portions of the aFGF are incorporated into the pBR322 plasmid. It is especially desired and intended that there be included within the scope of this invention, the use of other plasmids into which the aFGF gene can be incorporated and which will allow the expression of the aFGF gene. Reannealed oligonucleotides, about 300 fmole and about 100 fmole of the recovered 231 base pair N-terminus, are each ligated to about 100 fmole of agarose gel purified about 3.9 kilo base (kb) EcoRI-BamHI pBR322 for the N-terminus. The 209 bp C-terminus is constructed in the same manner using BamHI-SalI pBR322. Ligation is carried out in a buffer containing about 25 mM Tris, about pH 7.8, about 1 mM DTT, about 10 mMMgCl$_2$, about 0.4 mM ATP, with about 1 unit of T4 DNA ligase for about 1 hour at about 20° C. Each half-gene ligated vector is used to transform competent bacterial cells, such as E. coli RR1 (Bethesda Research Laboratories, BRL) following suppliers procedures. The transformed cells are selected for growth in ampicillin and screened for the presence of either the 231 base pair (bp) EcoRI-BamHI insert or the 209 bp BamHI-SalI insert by restriction analysis of mini-lysate plasmid preparations.

The DNA sequence of clones containing the appropriate sized inserts is determined using Maxam and Gilbert, Proc. Natl. Acad. Sci. USA 74: 560–564 (1977) chemical DNA sequence techniques.

The final full-length aFGF synthetic gene was cloned by cleaving the N-terminal half clone with restriction enzymes BamHI and SalI, treating with alkaline phosphatase and ligating this to the gel purified 209 bp BamHI-SalI insert of the C-terminal half clone. This ligated material was used to transform competent RR1 cells as before.

Expression of the synthetic aFGF gene is accomplished by a number of different promoter-expression systems. It is desired and intended that there be included within the scope of this invention the use of other promoter-expression systems for the expression of the intact aFGF gene. The preferred construct uses the E. coli tac promoter, a hybrid between regions of the trp promoter and the lac promoter as described by deBoer et al., Proc. Nat. Acad. Sci. USA 80: 21–25 (1983). Plasmid pKK 223-3 (Pharmacia) which contains the tac promoter and rrnB rRNA transcription terminator was modified to remove the pBR322-derived SalI restriction enzyme site. The rrnB rRNA terminator has been shown to allow expression by strong promoters, Gentz et al., Proc. Natl. Acad. Sci. USA 78: 4936–4940 (1981); Brosius, Gene 27: 161–172 (1984).

Figure 3:
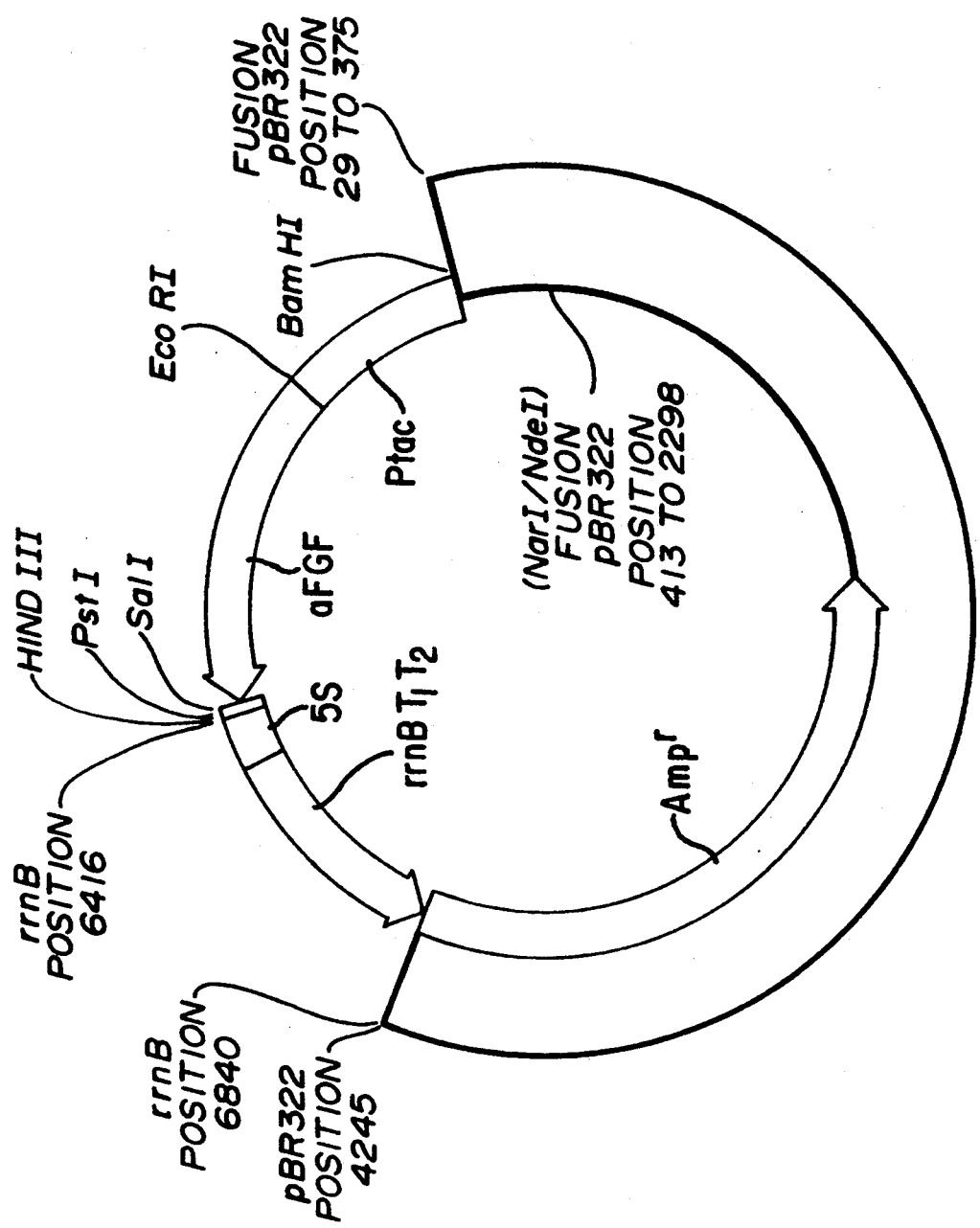
FIG. 3 is a diagram of the pKK223-3 plasmid containing a gene for either bovine or human aFGF.

The pKK223-3 plasmid DNA is cleaved with restriction enzymes to produce a 2.7 kb DNA fragment to generate clone pKK 2.7. The synthetic aFGF gene is cleaved from its pBR322 vector and transferred to the pKK 2.7 plasmid after restricting pKK 2.7 with EcoRI and SalI. The resulting recombinant, shown in FIG. 3, is transformed into E. coli JM105 (Pharmacia) or DH5 (BRL) cells and expressed.

Site specific mutagenesis is an efficient way to convert the amino acid sequence of one mammalian species of aFGF to the aFGF amino acid sequence of another species. The following description relates to the site specific mutagenic conversion of bovine aFGF, 140 amino acid form, to human aFGF, it is to be understood, however, that the process can be used to convert any mammalian species aFGF to that of any other species. The only limitation on the conversion is that the amino acid sequences of both aFGFs must be known. The following table lists the amino acids which must be substituted and the location on the bovine aFGF amino acid map, Table 3, at which the substitutions are made:

TABLE 5

| Amino Acid Location | Substituted Amino Acids | |
|---|---|---|
| | Human aFGF | for Bovine aFGF |
| 5 | Pro | Leu |
| 21 | His | Tyr |
| 35 | Arg | Lys |
| 47 | Ser | Cys |
| 51 | Val | Ile |
| 64 | Tyr | Phe |
| 106 | Asn | His |
| 116 | Ser | Arg |
| 117 | Cys | Ser |
| 119 | Arg | Leu |
| 125 | Tyr | Phe |

As with the bovine gene sequence eight oligonucleotides representing the human gene sequence are constructed by the same procedure as that used for the bovine oligonucleotides. The following table contains one of a multitude of oligonucleotide arrangements that is used to produce the human aFGF gene.

TABLE 6

OLIGO-1
5' CTGCCACCGGGTAATTAC 3'
OLIGO-2
5' CGGTGGTCACTTTCTCCG 3'
OLIGO-3
5' CGGCACCAGAGATCGTTC 3'
OLIGO-4
5' GCAGCTGTCCGCCGAATCTGTCGGTGAAG 3'
OLIGO-5
5' CTGGTCAATACCTTGCCATGG 3'
OLIGO-6
5' GCTGAGAAAAATTGGTTCG 3'
OLIGO-7
5' GGCCGCGTTTACAGCTGCCATTTTTCTTAAGG 3'
OLIGO-8
5' CGTACTCACTATGGCCAAAAAGCTATCC 3'

The cloned synthetic bovine gene for aFGF is converted to a human synthetic gene for aFGF by a series of directed point mutations. Oligonucleotide-directed mutagenesis of the cloned gene allows the alteration of the base sequence of bovine aFGF so that the resulting amino acid sequence contains the substituted amino acids shown in Table 5 and is human aFGF. A deletion is made in the bovine gene to remove the amino terminal phenylalanine for the production of the human 139 amino acid microheterogeneous form of aFGF. A point mutation is carried out to replace the second position asparagine with aspartic acid. The methods for carrying out these procedures are described below or are known in the art. Alternatively, the asparagine is chemically deamidated to aspartic acid. The oligonucleotide-directed mutagenesis is carried out using standard procedures known to the art, Zoller and Smith, Methods in Enzymology, 100: 468–500 (1983); Norris et al., Nucleic Acids Research, 11: 5103–5112 (1983); and Zoller and Smith, DNA, 3: 479–488 (1984). The point mutations carried out by the standardized oligonucleotide-directed mutagenesis are shown in the following, Table 7. The location of the base mutagenesis can be seen in Table 3. The point mutations are presented merely as an example of changes which will result in the human aFGF gene and should not be construed as limiting thereto.

TABLE 7

| Base Location | Substituted Base | | Corresponding Human Amino Acid |
|---|---|---|---|
| | Human aFGF | for Bovine aFGF | |
| 22 | C | T | Pro |
| 69 | C | T | His |
| 112 | G | A | Arg |
| 148 | C | G | Ser |
| 159 | G | A | Val |
| 199 | A | T | Tyr |
| 324 | A | C | Asn |
| 354 | A | C | Ser |
| 358 | G | C | Cys |
| 364 | G | T | Arg |
| 365 | C | G | Arg |
| 382 | A | T | Tyr |

The expression clones are grown at about 37° C. in an appropriate growth medium, which consists of about 1% tryptone, about 0.5% yeast extract, about 0.5% NaCl, about 0.4% glucose and about 50 μg/ml ampicillin. When the optical density at 550 nm reaches about 0.5, isopropyl-β-D-thiogalactopyranoside (IPTG) may be added to give a final concentration of about 1 mM and growth is continued at about 37° C. for about 3 hours. The cells from 1 liter of culture medium are harvested by centrifugation and resuspended in a disruption buffer containing about 10 mM sodium phosphate at about pH 7.2, about 5 mM EDTA, about 10.6 μg/ml N-p-toluenesulfonyl-L-phenylalanine chloromethyl ketone (TPCK), about 34.3 μg/ml pepstatin A, about 87 μg/ml phenylmethylsulfonyl fluoride (PMSF), about 15 μg/ml bovine pancreatic trypsin inhibitor (BPTI), and about 25.2 μg/ml leupeptin. The cells are either immediately disrupted or frozen and stored at −70° C. and disrupted immediately after thawing by about three passages through a French pressure cell at about 12,000 psi at about 4° C. The supernatant fluid is collected by centrifugation.

The recombinant aFGF is purified to homogeneity by a unique two-step chromatographic procedure employing a combination of heparin-Sepharose affinity chromatography followed by reversed-phase high performance liquid chromatography (HPLC). The crude r-aFGF is loaded onto a heparin-Sepharose column in a dilute buffer such as about 10 mM phosphate or Tris, about pH 6 to 8, which is subsequently washed with a low concentration of salt, such as about 0.8M NaCl, until the absorbance at 280 nm drops to about background. The r-aFGF is eluted with a buffered high salt concentration solution such as about 10 mM sodium phosphate or Tris, about pH 6 to 8, containing about 1.5M NaCl. The eluate is then purified by reversed-phase HPLC on a resin consisting of covalently linked alkyl silane chains with alkyl groups having from 3 to 18 carbon atoms, preferably 4 carbon atoms. The r-aFGF is directly applied to the HPLC column equilibrated in a dilute acid such as about 10 mM trifluoroacetic acid, acetic acid or phosphoric acid and eluted with a linear gradient of organic solvent such as acetonitrile or ethanol. Bovine brain-derived aFGF was previously described to bind to both heparin-Sepharose by Maciag et al. Science 225: 932–935 (1984) and to reversed-phase HPLC columns by Thomas et al. Proc. Natl. Acad. Sci. USA 81: 357–361 (1984) as part of multi-step purification protocols. Based, in part, on the relatively high abundance of r-aFGF in bacterial lysates, these two steps alone are herein demonstrated to be sufficient to obtain homogeneously pure r-aFGF of about 16,000 daltons as established by electrophoresis in polyacrylamide gels. These two steps alone do not yield pure aFGF from brain.

Mitogenic activity of the purified r-aFGF is determined by the incorporation of $^3$H-thymidine into DNA by cell line fibroblasts, preferably BALB/c 3T3 A31 (American Type Culture Collection). The recombinant aFGF shows a peak response at about 1 ng protein or less per ml in the fibroblast stimulative assay.

Recombinant and purified native aFGF is useful in promoting the healing of, but not limited to, soft tissue wounds resulting from burns, cuts or lacerations, and cutaneous ulcerations along with musculo-skeletal wounds such as bone fractures, ligament and tendon tears, and inflammation of bursas and tendons. Tissue repair as used herein is defined as the regeneration of tissue following the stimulation of cells by aFGF. Recombinant and purified native aFGF is also useful in promoting the healing and regeneration of cartilage and cartilaginous tissue. Administration of aFGF or r-aFGF for soft tissue repair will generally be by topical application. The novel peptide may be administered with or without heparin, preferably with heparin, about 0.1 to about 100 μg/cm²/day of the protein to the wound area either topically or subcutaneously. The most preferred application range for topical administration is about 1 to about 10 μg/cm²/day.

Heparin is a sulfated glycosaminoglycan consisting of equal parts of the sugars D-glucosamine and D-glucuronic acid which are sulfated to varying degrees. It is commercially available in unmodified form as well as in a solution form for direct therapeutic utilization. When heparin is administered with aFGF in topical or subcutaneous applications the preferred concentration is from about 3 times to about 30 times the amount of aFGF administered per day.

For topical application, various pharmaceutical formulations are useful such as ointments, pastes, solutions, gels, solid water soluble polymers such as albumins, collagens and gelatins, hydroxypropyl cellulose, pluronics, tetronics or alginates in which the active ingredient is incorporated in amounts of about 1 to about 100 μg/ml.

For musculo-skeletal healing, the native aFGF and r-aFGF is preferably administered at the site of the injury either during surgery or by injection. Surgical implantation of slow-release forms of the aFGF will allow for a continued release of the growth factor for a prolonged period of time. Methods of formulation of proteins such as aFGF for slow release are known in the art. Dosage levels for musculo-skeletal healing will be similar to those formulations used for soft tissue repair.

The ability of aFGF and r-aFGF to stimulate division in various cell types including fibroblasts, vascular and corneal endothelial cells and the like makes these peptides useful as pharmaceutical agents. These compounds can be used to treat wounds of mammals including humans by the administration of the novel proteins to patients in need of such treatment.

The novel method for the stimulation of vascular endothelial cells comprises treating a sample of the desired vascular endothelial cells in a nutrient medium with mammalian aFGF, preferably human or bovine, at a concentration of about 1–10 ng/ml.

If the vascular endothelial cell growth is conducted in vitro, the process requires the presence of a nutrient medium such as Dulbecco's modified Eagle's medium or modification thereof and a low concentration of calf or bovine serum such as about 0 to 2% by volume. Preservatives such as a penicillin-streptomycin combination or other broad spectrum antibacterials are also employed. It is preferred to have about 10 to 100 ug/ml of heparin present also.

The novel method of this invention is useful for the coverage of artificial blood vessels with endothelial cells. Vascular endothelial cells from the patient would be obtained by removal of a small segment of peripheral blood vessel or capillary-containing tissue and the desired cells would be grown in culture in the presence of aFGF and any other supplemental components that might be required such as heparin and/or serum. After growth of adequate numbers of endothelial cells in culture to cover the synthetic polymeric blood vessel the cells would be plated on the inside surface of the vessel which is then implanted in the patient. Alternatively, tubular supports are coated in vitro with aFGF prior to implantation into a patient. Following implantation endothelial cells migrate into and grow on the artificial surface. Prior coating of the artificial vessel either covalently or noncovalently, with either heparin or proteins such as fibrin, collagen, fibronectin or laminin would be performed to enhance attachment of the cells to the artificial vascular surface. The cell-lined artificial vessel would then be surgically implanted into the patient and, being lined with the patients own cells, would be immunologically compatible. The non-thrombogenic endothelial cell lining should decrease the incidence of clot formation on the surface of the artificial vessel and thereby decrease the tendency of vessel blockage or embolism elsewhere.

The novel method is also useful for the production of artificial vessels. Vascular endothelial cells and smooth muscle cells from the patient would be obtained and grown separately in culture. The endothelial cells would be grown in the presence of the aFGF as outlined above. The smooth muscle cells would be grown in culture by standard techniques. A tubular mesh matrix of a biocompatible polymer (either a synthetic polymer, with or without a coating of either heparin or specific attachment proteins, or a non-immunogenic biopolymeric material such as surgical suture thread) would be used to support the culture growth of the smooth muscle cells on the exterior side and vascular endothelial cells on the interior surface. Once the endothelial cells form a confluent monolayer on the inside surface and multiple layers of smooth muscle cells cover the outside, the vessel is implanted into the patient.

The novel method can also be used for the induction of tissue repair or growth. The pure growth factor of human, bovine or other origin would be used to induce and promote the repair or growth of tissue, including blood vessels, in the patient. The mitogen would be administered along with any necessary stabilizers and enhancers of activity including heparin, intravascularly to induce repair or at the site of desired vascular growth. For applications involving neovascularization and healing of surface wounds, such as abrasions or burns, the formulation would be applied directly at a rate of about 10 ng − 1 mg/cm²l/day of injured surface. The preferred application range for tissue repair is about 100 ng to about 100 μg per cm²l/day with the most preferred application range being about 1 to about 10 μg per cm²l/day. For vascular repair aFGF plus herparin is given intravenously at a rate of about 10 pg to about 1 μg/kg/day body weight for aFGF and heparin given at a rate of about 1 to 10 times the amount for aFGF. The preferred application range of aFGF for vascular repair is about 0.1 to about 100 ng/Kg/day with the most preferred application range being about i to about 10 ng/Kg/day. For internal vascular growth, the formulation would be released directly into the region to be neovascularized either from implanted slow release polymeric material or from slow release pumps. The release rate in either case is about 100 ng to about 100 μg/day/cm³ or preferably about 100 ng to about 10 μg/day/cm³ of injured tissue.

The following examples illustrate the invention but are not to be construed as limiting.

EXAMPLE 1

Purification of Native Bovine and Human aFGF

Bovine and human brain-derived aFGF was initially purified by the salt precipitations and CM-Sephadex C-50 ion exchange chromatography as described in U.S. Pat. No. 4,444,760. The material eluted from the C-50 ion exchange column was dialyzed against 10 mM Tris-HCl containing 0.6M NaCl, pH 7.0, and loaded on a heparin-Sepharose column equilibrated in the same buffer. The column was washed extensively with buffer containing 0.8M NaCl, and eluted with a 1.5M NaCl buffer solution. The eluant was further purified by $C_4$ high performance liquid chromatography following the technique of Thomas, U.S. Pat. No. 4,444,760.

EXAMPLE 2

Peptide Generation and Purification

The purified bovine and human aFGFs from Example 1 were cleaved and sequenced. Tryptic peptides were generated from 1.3 nmoles of lyphilized carboxymethylated aFGF with a 1:100 mass ratio of L-(tosylamido-2-phenyl)ethyl chloromethyl ketone-treated bovine pancreatic trypsin (Worthington) to aFGF in 200 μl of 0.1M ammonium bicarbonate (pH 8.3) at 37° C. for 6 hours and purified by acetonitrile gradient elution from a 330 A pore size, 5 μm particle size, 4.6 mm×25 cm Vydac $C_{18}$ reversed-phase HPLC column.

Cleavage on the carboxyl terminal side of Glu residues was performed on 1.3 nmoles of lyophilized carboxymethylated aFGF, solubilized in 10 μl of 10 mM HOAc, with a 1:30 mass ratio of *Staphylococcus aureus* V8 (Miles) to substrate protein in 150 μl of 0.1M ammonium bicarbonate, pH 7.8 (BDH AnalaR), 2 mM EDTA, 0.36M guanidinium chloride. The pH was chosen to minimize the extent of cleavage of peptide bonds following Asp residues. Digestion was performed at 37° C. for 24 hours and the peptides purified by HPLC chromatography as described above.

Methionine sulphoxide residues in carboxymethylated aFGF (2.6 nmol) were reduced to methionine residues in 250 μl of 2M dithiothreitol, 0.1M NaOAc, pH 6.9 at 39° C. for 21 hours (19), loaded on a 330 A pore size, 5 μm particle size, 4.6 mm×5 cm $C_4$ reversed phase HPLC column (Vydac) equilibrated in 10 mM trifluoroacetic acid (TFA), eluted with a 15 minute linear gradient to 3.3 mM TFA, 67% by volume acetonitrile at 0.5 ml/minute and lyophilized. The aFGF product was cleaved at the peptide bond following the single Met residue with a 6,800-fold molar excess of cyanogen bromide in 200 μl of 70% formic acid. The reaction vial was flushed with argon, sealed and incubated in the dark at 20° C. for 24 hours. The products were purified by HPLC chromatography as described for the tryptic peptides above.

The complete protein and constituent pure peptides were sequenced on Polybrene-coated filters using an Applied Biosystems 470A microsequencer. Phenylthiohydantoin amino acid derivatives generated from the sequence analysis by methanolic.HCl conversion were identified on a Zorbax PTH column (DuPont) and quantitated using a Kratos 783 flow spectrophotometer with a Nelson 4400 recording integrator. PTH-[$^{14}$C]-carboxymethyl Cys residues from the amino terminal degradation and sequence determinations of radioactive peptides were confirmed by scintillation counting ⅓ of the PTH derivatives. Repetitive yields were equal to or greater than 93%.

Carboxymethylated aFGF (1.3 nmoles) was digested with carboxypeptidase A (80 pmoles, Worthington) in 80 μl of 0.2M ammonium acetate buffer, pH 6.0 at 38° C. Aliquots (9 ul) were taken at intervals up to 48 hours, derivatized with phenylisothiocyanate and released carboxy terminal residues identified by chromatography on a 4.6 mm×25 cm Zorbax $C_{18}$ (DuPont) HPLC column.

The complete amino acid sequence of bovine aFGF is shown in FIG. 1 while the complete amino acid sequence of human aFGF is shown in FIG. 2. The abbreviations; T, CNBr, HA and V8 refer to tryptic, cyanogen bromide, hydroxylamine and *Staphylococcus aureus* V8 protease generated peptides respectively.

EXAMPLE 3

Oligonucleotide Synthesis

Oligonucleotides were synthesized according to the technique described by Matteucci and Caruthers, J. Am. Chem. Soc. 103: 3185–3191 (1981); Beaucage and Caruthers, Tetrahedron Letters 22: 1859–1862 (1981). The base sequences of the synthesized oligonucleotides are shown in Table 4.

EXAMPLE 4

Assembly of the aFGF Gene

The oligonucleotides from Example 3 were assembled as two separate units, the N-terminal half (231 bp) and the C-terminal half (209 bp). The two halves were then combined for the intact synthetic gene, see Table 3. Initially the oligonucleotides were kinased in the following reaction mixture: 70 mM Tris pH 7.6, 5 mM DTT, 10 mM MgCl$_2$, 33 μM ATP, 0.3 units T4 polynucleotide kinase per μl, and 2.5 pmole oligonucleotide per μl. The mixture was incubated 1.5 hours at 37° C. and then an additional hour after supplementing the mixture with 0.2 units/μl kinase and ATP to give a concentration of 100 mM. For radioactive labeling, the initial mixture contained 37 nCi/μl of [γ-$^{32}$P]-ATP.

The annealing and ligations were done in two separate reactions. In each reaction, 100 pmole of each of the eight oligonucleotides were added. In one reaction the oligonucleotides which make up one strand of the C-terminal or N-terminal half-gene were kinased with the exception of the most 5' oligonucleotide. In the second reaction the oligonucleotides which make up the opposite strand were kinased, again with the exception of the most 5' oligonucleotide. Thus, in each reaction 3 oligonucleotides were kinased and 5 were not. When kinased oligonucleotides were used, 1 pmole of the $^{32}$P-labelled oligonucleotide was also added for later identification of the products. Each reaction contained 200 μl with 70 mM Tris pH 7.6, 5 mM DTT, 10 mM MgCl$_2$, and 30 μM ATP. The oligonucleotides were annealed by heating to 90° C. for 4 minutes, then immediately transferring the reaction to 60° C. and allowing it to cool slowly to 30° C. Ligation was done in 400 μl containing 60 mM Tris pH 7.6, 10 mM DTT, 10 mM MgCl$_2$, 1 mM ATP, and 0.03 units T4 DNA ligase per μl by incubating at 20° C. for 1.5 hours.

Polyacrylamide gel electrophoresis was used to purify the ligated oligonucleotides. The ligated oligonucleotides were precipitated with ethanol, redissolved in 20 μl of 80% formamide, 50 mM Trisborate pH 8.3, 1 mM EDTA, 0.1% (w/v) xylene cyanol, and 0.1% (w/v) bromophenol blue. Each sample was heated at 90° C. for 3 minutes and electrophoresed in a 10% urea-polyacrylamide gel at 75 watts for 5 hours. The oligonucleotide bands were visualized by exposing the gel to X-ray film.

The 231 base bands of each reaction for the N-terminus were cut out of the gel, combined, and eluted at 4° C. in 1 ml of 0.5M ammonium acetate, 1 mM EDTA pH 8. The eluted DNA was precipitated with ethanol and redissolved in 30 µl of 70 mM Tris pH 7.6, 5 mM DTT, and 10 mM MgCl$_2$. The 209 base bands of the C-terminus were eluted in the same manner.

The gel purified oligonucleotides were annealed prior to transformation by heating to 90° C. for 4 minutes and slow cooling to 20° C. Assuming a 5% recovery from the initial starting oligonucleotides, 300 fmole and 100 fmole of recovered annealed 231 bp oligonucleotides were each ligated to 100 fmole of agarose gel purified 3.9 kb EcoRI-BamHI pBR322 fragment DNA in 20 µl of 25 mM Tris pH 7.8, 1 mM DTT, 10 mM MgCl$_2$, 0.4 mM ATP, with 1 unit T4 DNA ligase for 1 hour at 20° C. The annealed 209 bp oligonucleotides were ligated to agarose purified 3.9 kb BamHI-SalI pBR322 fragment DNA under the same conditions as the 231 base pair fragments. The ligation reactions were diluted 1:5 in H$_2$O and 1 µl of dilution was used to transform 20 µl of competent E. coli RR1 cells (BRL) as described by the supplier. The transformants were selected for growth in ampicillin and screened for the presence of the 231 bp EcoRI-BamHI or the 209 bp BamHI-SalI insert by restriction analysis of mini-lysate plasmid preparations.

The DNA sequence of clones containing the appropriate sized inserts was determined using the chemical DNA sequence techniques of Maxam and Gilbert, Proc. Natl. Acad. Sci. USA 74: 560–564 (1977). Since none of the 231 bp clones had the correct sequence, a clone containing the correct sequence was prepared as follows. One clone with the correct sequence between the KpnI and BamHI sites was cleaved with KpnI and with SalI, which cleaves in the pBR322 vector. The 400 bp band was gel purified and ligated to the 3.8 kb KpnI-SalI band of a second clone containing the correct sequence from the EcoRI site to the KpnI site of the aFGF gene insert. After transformation, a resulting clone was sequenced to ensure the desired sequence had been obtained.

Since a clone containing the correct 209 bp sequence was obtained, no further manipulation of these clones was required. The final full-length aFGF synthetic gene was cloned by cleaving the N-terminal half clone with BamHI and SalI, treating with alkaline phosphatase, and ligating this to the gel purified 209 bp BamHI-SalI insert of the C-terminal half clone. This ligated material was used to transform competent RR1 cells as before.

EXAMPLE 5

Expression of the Synthetic Bovine aFGF Gene

The intact aFGF gene from Example 4 was incorporated into a modified pKK223-3 plasmid. The pKK223-3 plasmid (Pharmacia) contains the tac promoter which is a hybrid between regions of the trp promoter and the lac promoter, deBoer et al., Proc. Natl Acad. Sci. USA 80: 21–25 (1983). This plasmid also contains the rrnB rRNA transcription terminator, a strong terminator sequence found to allow expression from strong promoters, Gentz et al., Proc. Natl. Acad. Sci. USA 78: 4936–4940 (1981); Brosius, Gene 27: 161–172 (1984). The pKK 223-3 plasmid was modified to remove the pBR322-derived SalI restriction enzyme site. This was accomplished by cleaving the pKK223-3 plasmid DNA with NdeI and NarI, and recircularizing the 2.7 kb DNA fragment to generate clone pKK2.7. The synthetic aFGF gene was then cleaved from its pBR322 vector and transferred to pKK2.7 after restricting this expression vector with EcoRI and SalI. This construction positions the initiating methionine of the synthetic gene 11 bases downstream of the Shine-Dalgarno ribosome binding site. The resulting recombinant, shown in FIG. 3, was transformed into E. coli JM105 cells and also into E. coli DH5 cells.

The expression clones were grown at 37° C. in LB broth (1% tryprone, 0.5% yeast extract, 0.5% NaCl) containing 0.4% glucose and 50 µg/ml ampicillin. When the optical density at 550 nm reached 0.5, IPTG was added to give 1 mM and growth was continued at 37° C. for 3 hours. The cells were harvested by centrifugation at 10,000×g for 20 minutes and the cells from 1 liter of culture were resuspended in 20 ml of 10 mM sodium phosphate pH 7.2, (heparin-Sepharose buffer) 5 mM EDTA, 10.6 µg/ml TPCK, 34.3 µg/ml pepstatin A, 87 µg/ml PMSF, 15 µg/ml BPTI, and 34.3 µg/ml leupeptin. The resuspended cells were quickly frozen in a dry ice/ethanol bath and stored overnight at −70° C.

EXAMPLE 6

Extraction and Purification of Recombinant aFGF

The frozen cells from Example 5 were thawed, an additional 87 µg/ml PMSF was added, and the preparation was passed through a French pressure cell at 12,000 psi three times at 4° C. The resulting lysate was centrifuged at 93,000×g for 30 minutes to remove cell debris. The supernatant was removed, adjusted to pH 7.2 with 1M NaOH and loaded onto a 1.6×b 10 cmheparin-Sepharose (Pharmacia) column run at 4° C. with a flow rate of 20 ml per hour collecting 2 ml fractions. The pellet was resuspended in 5 ml of 10 mM sodium phosphate, 2M NaCl, pH 7.2, recentrifuged at 93,000×g for 30 minutes and the supernatant diluted with three volumes of 10 mM sodium phosphate, pH 7.2, readjusted to pH 7.2 with 1M NaOH, if necessary, and loaded onto the same heparin-Sepharose column. After loading, the column was washed with 10 mM sodium phosphate, 0.8M NaCl, pH 7.2 until the absorbance at 280 nm fell to background. Bound r-aFGF was eluted as a single peak with 10 mM sodium phosphate, 1.5M NaCl, pH 7.2. The pooled fractions from the heparin-Sepharose column were purified by reversed-phase HPLC using a 4.6 mm×25 cm C$_4$ column (Separations Group) as described by Thomas et al., Proc. Natl. Acad. Sci. USA 81: 357–361 (1984). The r-aFGF eluted as a single major peak that was resolved from multiple minor contaminant peaks suggesting that the protein was homogeneously pure. Polyacrylamide gel electrophoresis was used to confirm purity. The purified and reduced r-aFGF was electrophoresed with sodium dodecylsulfate in a 15% polyacrylamide gel following reduction following the technique of O'Farrell, J. Biol. Chem. 250: 4007–4021 (1975). Silver staining revealed a single band with a molecular mass of 16,000 daltons. Identity of the protein as aFGF was confirmed by both amino acid analysis and amino terminal sequence determination.

EXAMPLE 7

Biological Activity of Bovine Recombinant aFGF

Biological activity of the purified r-aFGF from Example 6 was evaluated using a fibroblast mitogenic assay as described by Thomas et al., J. Biol. Chem. 225: 5517–5520 (1980). BALB/c 3T3 A31 fibroblasts (American Type Culture Collection) were plated at 2×10$^4$ cells per 35 mm diameter well in culture media containing 10% heat-inactivated calf serum and incubated in 7% $CO_2$ (pH 7.35±0.05). The cells became fully quiescent by replacing the media with 0.5% heat-inactivated calf serum 6 and again 24 hours later. At 55 hours after plating, 50 μg of heparin, test samples and 1.1 μg of dexamethasone were added, at 70 hours each well was supplemented with 2 μCi of [methyl-$^3$H]-thymidine (20 Ci/mmole, New England Nuclear) and 3 μg of unlabeled thymidine (Sigma), and at 95 hours the cells were processed for determination of radiolabel incorporated into DNA. Each dose-response point was the average of triplicate determinations. The results are shown in the following table:

TABLE 8

Mitogenic Responses of BALB/c 3T3 Fibroblasts to Bovine r-aFGF

| Concentration r-aFGF (ng/ml) | CPM r-aFGF | Brain aFGF |
|---|---|---|
| 0.003 | 268 | 231 |
| 0.010 | 498 | 329 |
| 0.031 | 1550 | 1017 |
| 0.100 | 7031 | 3684 |
| 0.316 | 9319 | 11353 |
| 1.000 | 4718 | 9050 |

The activity of the recombinant aFGF was equal to or slightly greater than that of brain derived aFGF. The purified r-aFGF had a half-maximal stimulation of DNA synthesis at about 71 pg/ml while purified brain derived aFGF had a half-maximal value 126 pg/ml.

EXAMPLE 8

Mutagenesis of the Bovine aFGF Gene to the Human aFGF Gene

To facilitate the mutagenesis of the bovine aFGF gene, the synthetic gene from Example 4 was transferred to M13mp19, a single-stranded DNA bacteriophage vector. Standard mutagenesis procedures were used as reported by Zoller and Smith, Methods in Enzymology, 100: 468–500 (1983); Norris et al., Nucleic Acids Research, 11: 5103–5112 (1983); and Zoller and Smith, DNA, 3: 479–488 (1984). The bovine pKK-aFGF plasmid was cleaved with EcoRI and SalI, see Table III, and the resulting 440 bp fragment was agarose gel purified as in Example 2. Vector M13mp19 RF DNA (BRL) was cleaved with the same two endonucleases and the ends were subsequently dephosphorylated in 100 μl of 10 mM Tris. pH 8.0 buffer with 100 units of bacterial alkaline phosphatase. A ligation was performed using 50 ng of the treated vector DNA and 12 ng of the aFGF gene fragment DNA in 10 μl of 25 mM Tris pH 7.8, 10 mM $MgCl_2$, 1 mM DTT, 0.4 mM ATP, with 2 units of T4 DNA ligase for 16 hours at 4° C. The reaction mixture was diluted 1:5 in $H_2O$ and 1 μl of dilution was used to transform 20 μl of competent E. coli DH5 cells (BRL) as described by the supplier. The cells were plated with E. coli JM105 (Pharmacia) host cells in 0.03% X-gal and 0.3 mM IPTG; after incubation at 37° C. colorless plaques were isolated. One phage clone containing the bovine aFGF gene was selected, M13mp19-aFGF.

Eight oligonucleotides were designed to specify the human sequence and synthesized, see Table 6.

Oligmer 8 contains an additional mutation in which thymine at site 386 in the bovine gene is replaced by cytosine in the human gene. This mutation allows the incorporation of a restriction site without altering the human aFGF amino acid sequence.

The human oligomers 1, 2, 3, 4, 6, and 8 were phosphorylated and 15 pmoles of each were annealed individually to 0.5 pmole of M13mp19-aFGF single-stranded phage DNA in 10 μl of 20 mM Tris pH 7.5, 10 mM $MgCl_2$, 50 mM NaCl, 1 mM DTT for 10 minutes at 65° C. followed by 10 minutes at 23° C. Closed-circular double-stranded molecules were then prepared in 20 μl of 20 mM Tris PH 7.5, 10 mM $MgCl_2$, 25 mMNaCl, 5.5 mM DTT, 0.5 mMATP, 0.25 mM dATP, 0.25 mM dCTP, 0.25 mM dCTP, 0.25 mM dGTP, 0.25 mM dTTP, using 1 unit of T4 DNA ligase and 2 units of DNA polymerase I klenow fragment by incubation at 15° C. for 17 hours. The preparations were each used to transform competent JM105 cells and the resulting transformant plaques were selected by hybridization with the appropriate oligomer which had been radiolabeled using $^{32}$P-ATP and polynucleotide kinase. The conditions of hybridization were optimized for each probe to prevent formation of hybrids containing single base changes. Single-stranded DNA was isolated from the phage clone containing the human oligomer 4 mutations and the above procedure was repeated using the human oligomer 5 to generate a clone containing both the oligomer 4 and 5 mutations.

In the following procedures the bovine-to-human sequence mutations in these M13-based clones were combined into one pBR322-based clone. RF DNAs were prepared from clones containing the base changes specified by human oligomers 1, 2, 6, and 8. The DNA of the human 1 mutant clone was cleaved with EcoRI, the ends were dephosphorylated with bacterial alkaline phosphatase, and the DNA was cleaved with HindIII. The human 2 mutant DNA was cleaved with HindIII, treated with phosphatase, and then cleaved with BamHI. The human 6 mutant DNA was cleaved with BamHI, phosphatase treated, and subsequently cleaved with ApaI. Likewise, the human 8 mutant DNA was cleaved with ApaI, the ends were dephosphorylated, and the DNA was cleaved with SalI. These four DNA preparations were electrophoresed through 2% agarose and the fragments of 45 bp, 190 bp, 135 bp, and 70 bp from the mutant DNAs containing human 1, 2, 6, and 8 mutations, respectively, were eluted from the gel. Approximately 60 fmoles of each fragment were collectively ligated to about 60 fmoles of a gel-purified 3.7 kb EcoRI-SalI fragment from pBR322 in 5 μl of 25 mM Tris pH 7.8, 10 mM $MgCl_2$, 1 mM DTT, 0.4 mM ATP, with 1.5 units of T4 DNA ligase for 16 hours at 12° C. The reaction mixture was diluted 1:5 in $H_2O$ and 1 μl of dilution was used to transform 20 μl of competent E. coli DH5 cells (BRL) as described by the supplier. A clone containing the mutations specified by all four mutant oligomers was selected by hybridization with radiolabeled probes prepared from each of the oligomers. The 140 bp KpnI-BamHI DNA fragment isolated from cleaved RF DNA of the human 3 mutant M13 clone was ligated to endonuclease cleavage products of this human 1-2-6-8 mutant DNA and transformed into DH5 competent cells to generate a clone with the human 1-2-3-6-8 mutations. BamHI-PstI digestion fragments of this latter clone were ligated to the BamHI-PstI digestion fragments of RF DNA from the human 4-5 M13-based clone and the ligation mixture was used to transform DH5 competent cells. A clone containing the human 1-2-3-4-5-6-8 mutations was selected by oligomer hybridization and the aFGF gene EcoRI-SalI DNA fragment of this recombinant plasmid was ligated to phosphatase-treated EcoRI-SalI-cleaved RF DNA of M13mp18 (BRL). Competent DH5 cells were transformed with this ligated DNA and the transformed cells were plated on JM105 host cells to generate an M13 clone. The single-stranded phage DNA of this clone was annealed with the human 7 oligomer and an M13 clone containing all the desired mutations was obtained following the procedure described above. RF DNA was prepared from this clone and cleaved with EcoRI and SalI. The resulting 440 bp band was gel purified and ligated to the 2.7 kb EcoRI-SalI DNA fragment of the pKK2.7 tac promoter expression vector. This DNA was used to transform competent DH5 cells thus generating the human pKK-aFGF expression clone used for production of the human form of aFGF.

The human r-aFGF was purified by the same procedure as that used for the bovine r-aFGF, see Example 6. The human r-aFGF was judged to be at least 99.75% pure based on the presence of a single intense band on a silver stained SDS electrophoretic gel loaded with 400 ng of purified human r-aFGF and having a sensitivity of about 1 ng/band. The protocol is described in Example 6.

The pure recombinant human aFGF was assayed for mitogenic activity using $^3$H-thymidine incorporation into subconfluent BALB/c 3T3 cells as described for the bovine recombinant protein in Example 7. As previously observed with human brain-derived aFGF assayed on vascular endothelial cells, the recombinant human protein shows a greater difference in the heparin (50 μg/ml) activation than does either the brain-derived or recombinant bovine aFGF, Gimenez-Gallego et al. Blochem. Biophys. Res. Comm. 135: 541–548(1986); the results of recombinant human aFGF on Balb/c 3T3 cells are shown in the following table:

TABLE 9

Mitogenic Responses of BALB/c 3T3 Fibroblasts to Human r-aFGF.

| Concentration r-aFGF (picograms/ml)* | CPM − heparin | CPM + heparin |
|---|---|---|
| 0 | 3574 | 991 |
| 1 | 4156 | 1336 |
| 3.16 | 4216 | 1802 |
| 10.0 | 4092 | 2617 |
| 31.6 | 4155 | 4824 |
| 100 | 4274 | 10489 |
| 316 | 6060 | 14584 |
| 1000 (1 ng) | 6811 | 10547 |
| 3160 | 7910 | 12357 |
| 10000 | 8597 | 9143 |
| 31600 | 9700 | 9057 |
| 100000 | 11166 | 9277 |
| 1000000 (1 μg) | 15864 | 12425 |

*picogram = $10^{-12}$ grams

All dilutions were prepared from a stock solution containing 1.51 mg/ml of purified r-aFGF. In the presence of heparin, the half-maximal stimulation occurs at about 42 pg/ml. In the absence of heparin the peak has not clearly been reached even at the highest concentration but must be greater than about 30 ng/ml.

EXAMPLE 9

Mitogenic Response of Fetal Bovine Thoracic Aortic Endothelial Cells to aFGF

Figure 4:
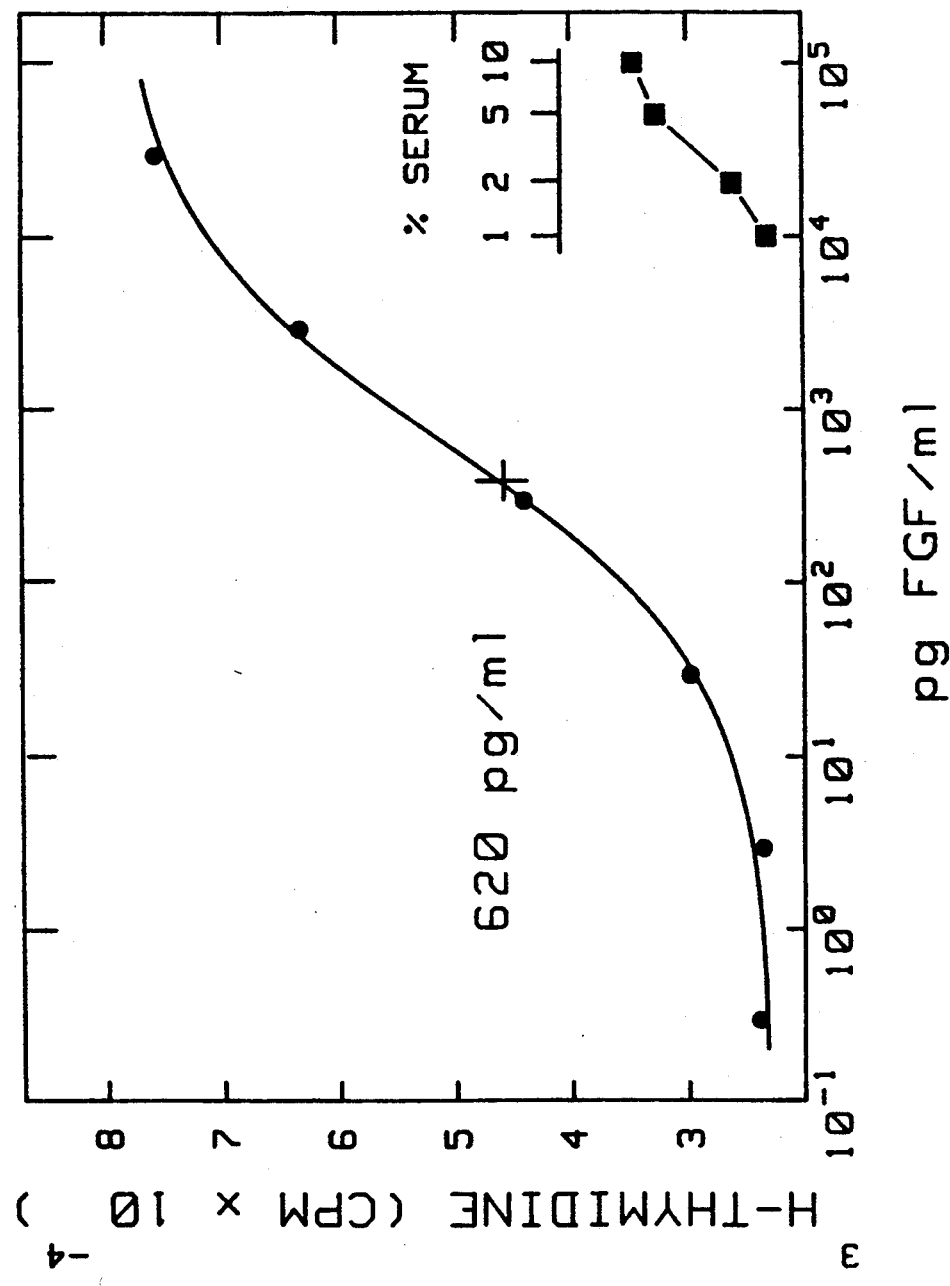
FIG. 4 is a diagram of the mitogenic response of fetal bovine thoracic aortic endothelial cells to aFGF.

Fetal bovine thoracic aortic endothelial cells (AG4762, N.I.A. Aging Cell Repository, Institute for Medical Research, Camden, N.J.) were assayed after 38 cumulative population doublings in vitro. The cells were plated in 6-well Costar plates at $2 \times 10^3$ cells/cm$^2$ in 20% heat inactivated fetal calf serum in Dulbecco's modified Eagle's medium (DMEM, Gibco) and changed to 1% serum 18 hours later. All media were supplemented with glutamine and penicillin-streptomycin as previously described. Either pure bovine aFGF from Example 1 diluted in 100 ul of 1 mg bovine serum albumin (Sigma) per ml of DMEM or serum samples were added to each well along with 1.6 uCi of $^3$H-thymidine (New England Nuclear) and 45 ug of unlabeled thymidine in 40 ul of DMEM. After a 48 hour incorporation period, the cells were washed, lysed and 75% of the trichloroacetic acid (TCA)-insoluble DNA from pure growth factor or serum-stimulated cells was counted. The increase in endothelial cell population at various concentrations of aFGF was measured by measuring the uptake of tritiated thymidine. The results are shown in FIG. 4 (the circles represent aFGF and the squares represent serum).

EXAMPLE 10

Mitogenic Response of Mouse Lung Capillary Endothelial Cells to aFGF

Figure 5:
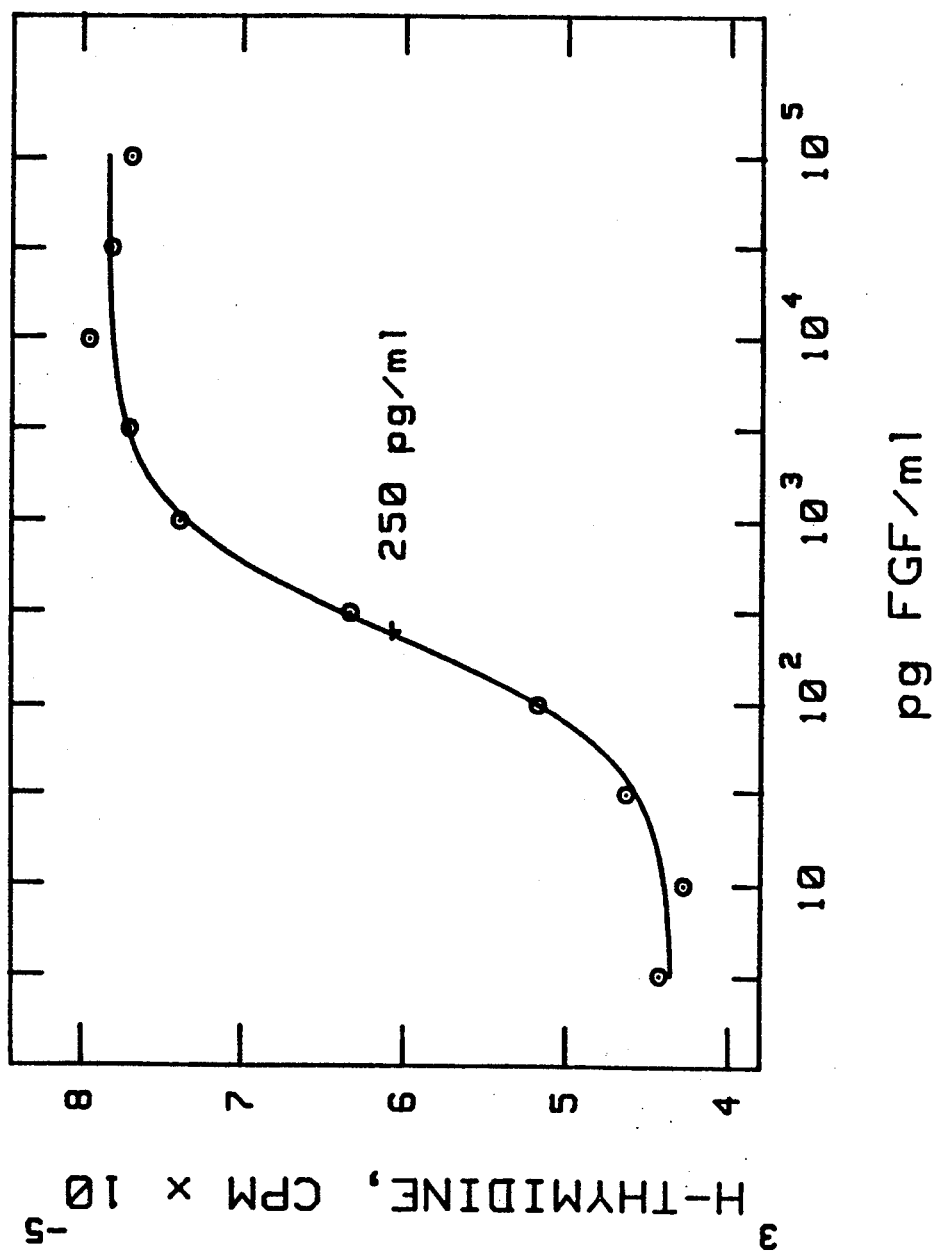
FIG. 5 is a diagram of the mitogenic response of mouse lung capillary endothelial cells to aFGF.

Mouse lung capillary endothelial cells were plated at $2.6 \times 10^4$ cells/cm$^2$ in 0.5 ml/well in 24-well Costar dishes and grown to confluence in 10% charcoal-treated calf serum (HyClone Laboratories, Logan, Utah) in DMEM, lowered to 0.5% serum after 72 hours and allowed to become quiescent over 48 hours. Either serum or the pure bovine or human aFGF from Examples 1, 6 and 8 added in 50 μl as described above followed 18 hours later by a 4 hour pulse of $^3$H-thymidine (20 ul of 100 uCi/ml $^3$H-thymidine in Gibco phosphate buffered saline). The cells were processed and radioactivity counted as described in Examples 7 or 9, and the results were as shown in FIG. 5.

EXAMPLE 11

Angiogenic Activity of aFGF Chicken Egg Angiogenesis Bioassay

During sustained vascular growth, endothelial cells are observed to actively proliferate. Therefore, we tested the ability of the purified aFGF from Example 1 to induce blood vessel growth in the chicken egg chorioallantoic membrane angiogenesis assay. Based on previous reports that crude tumor angiogenesis factor was significantly more active with coadministered heparin, we tested the vascularization response of heparin alone and heparin plus pure aFGF.

Three-day old chicken embryos were removed from their shells and grown in Handiwrap pouches suspended inside paper cups. The tops of the cups were covered with Handiwrap, and the eggs were incubated at 37° C. in a tissue culture incubator for 5–6 days. Either 1 μg of pure bovine aFGF in about 30 μl of the HPLC elution solvent (7 mM trifluoroacetic acid/33% acetonitrile) or an identical HPLC solvent control solution were mixed with an equal volume of 2% low-gelling temperature agarose (Miles) dissolved in lactated Ringer's solution (Abbott) containing 10 μg of heparin (from porcine intestinal mucosa; Sigma grade 1). Droplets (60 μl) were allowed to gel on the center of sterile plastic 1.3-cm diameter Thermanox tissue culture coverslips (Miles), and at least part of the volatile acetonitrile evaporated by aeration for 15–30 minutes under a plenum of sterile air in a tissue culture hood. The coverslips were positioned, pellet down, over the chorioallantoic membrane of the eggs and incubated for 3 days. Eggs containing large white focal regions under the coverslips at the end of the assay, presumably formed by inflammatory cells, were discarded. The chorioallantoic membranes were examined microscopically and scored for the proliferation of fine capillaries under the center of cover-slips by observers who did not know the contents of the agarose pellets.

A 10 μg dose of heparin per egg was inactive but the same amount of heparin plus 1 μg of aFGF per egg appeared to enhance the growth of small capillaries at the site of application with no sign of inflammation (Table 10). The assay is reproducible, the results being a composite of three separate assays with different samples of aFGF. Control and positive angiogenic responses show the extent of capillary proliferation induced by aFGF. The mitogen is, therefore, a potent angiogenic protein in the presence of heparin.

TABLE 10

| Angiogenic Activity of aFGF | | |
|---|---|---|
| | Angiogenic response | |
| Sample contents | Negative | Positive |
| Control | 15 | 0 |
| aFGF | 2 | 10 |

These data are a composite of three separate experiments. Using t-distribution statistics, the group of mitogen-stimulated eggs was calculated to be different from the control population with a confidence level of 99.9%.

What is claimed is:

1. An isolated and purified recombinant human acidic fibroblast growth factor characterized as a homogeneously pure protein which has a half-maximal mitogenic activity of about 40 picograms per mililiter and has an amino acid sequence of human acidic fibroblast growth factor selected from the group consisting of the 140 amino acid form and the 139 amino acid form of human acidic fibroblast growth factor, with said human acidic fibroblast growth factor being dependent upon the presence of heparin for said half-maximal mitogenic activity.

2. The human acidic fibroblast growth factor of claim 1 wherein said acidic fibroblast growth factor has the following amino acid sequence:

```
1                          10                              20
PheAsnLeuProProGlyAsnTyrLysLysProLysLeuLeuTyrCysSerAsnGlyGlyHisPheLeuArgIleLeu 30                 40                      50
ProAspGlyThrValAspGlyThrArgAspArgSerAspGlnHisIleGlnLeuGlnLeuSerAlaGluSerValGlyGlu 60                      70                              80
ValTyrIleLysSerThrGluThrGlyGlnTyrLeuAlaMetAspThrAspGlyLeuLeuTyrGlySerGlnThrProAsn 90                      100
GluGluCysLeuPheLeuGluArgLeuGluGluAsnHisTyrAsnThrTyrIleSerLysLysHisAlaGluLysAsnTrp 110                    120                    130
PheValGlyLeuLysLysAsnGlySerCysLysArgGlyProArgThrHisTyrGlyGlnLysAlaIleLeuPheLeuPro

140
LeuProValSerSerAsp
```

* * * * *